(12) United States Patent
Chirino et al.

(10) Patent No.: US 7,144,987 B1
(45) Date of Patent: Dec. 5, 2006

(54) PROTEIN BASED TUMOR NECROSIS FACTOR-RECEPTOR VARIANTS FOR THE TREATMENT OF TNF RELATED DISORDERS

(75) Inventors: Arthur J. Chirino, Camarillo, CA (US); Peizhi Luo, Arcadia, CA (US); Peter Colon McDonnell, Thousand Oaks, CA (US); Umesh Muchhal, West Covina, CA (US); Malu Lourdes Tansey, Coppell, TX (US)

(73) Assignee: Xencor, Monrovia, CA (US)

(*) Notice: Subject to any disclaimer, the term of this patent is extended or adjusted under 35 U.S.C. 154(b) by 595 days.

(21) Appl. No.: 10/336,242

(22) Filed: Jan. 3, 2003

Related U.S. Application Data

(63) Continuation-in-part of application No. 10/262,630, filed on Sep. 30, 2002, which is a continuation-in-part of application No. 09/981,289, filed on Oct. 15, 2001, now Pat. No. 7,101,974, and a continuation-in-part of application No. 09/945,150, filed on Aug. 31, 2001, now abandoned, and a continuation-in-part of application No. 09/798,789, filed on Mar. 2, 2001, now Pat. No. 7,056,695.

(60) Provisional application No. 60/186,427, filed on Mar. 2, 2000, provisional application No. 60/345,772, filed on Jan. 4, 2002, provisional application No. 60/415,545, filed on Oct. 1, 2002.

(51) Int. Cl.
  *C07K 17/00* (2006.01)
  *C07K 14/52* (2006.01)
  *C12N 15/00* (2006.01)

(52) U.S. Cl. .................... 530/351; 530/350; 435/69.5; 435/335; 435/7.1

(58) Field of Classification Search .................... None
  See application file for complete search history.

(56) References Cited

U.S. PATENT DOCUMENTS

| | | | |
|---|---|---|---|
| 5,344,915 A | 9/1994 | LeMaire et al. | |
| 5,395,760 A | 3/1995 | Smith et al. | |
| 5,478,925 A | 12/1995 | Wallach et al. | |
| 5,512,544 A | 4/1996 | Wallach et al. | |
| 5,605,690 A | 2/1997 | Jacobs et al. | |
| 5,610,279 A | 3/1997 | Brockhaus et al. | |
| 5,695,953 A | 12/1997 | Wallach et al. | |
| 5,712,155 A | 1/1998 | Smith et al. | |
| 5,808,029 A | 9/1998 | Brockhaus et al. | |
| 5,811,261 A | 9/1998 | Wallach et al. | |
| 5,925,548 A | 7/1999 | Beutler et al. | |
| 5,945,397 A | 8/1999 | Smith et al. | |
| 5,981,701 A | 11/1999 | Wallach et al. | |
| 6,271,346 B1 | 8/2001 | Hauptmann et al. | |
| 6,433,158 B1 * | 8/2002 | Pettit | 536/23.5 |

FOREIGN PATENT DOCUMENTS

| | | |
|---|---|---|
| EP | 0 433 900 A1 | 6/1991 |
| EP | 0 526 905 A2 | 2/1993 |
| JP | 03-133382 | 6/1991 |
| JP | 03-163099 | 7/1991 |
| JP | 10-191986 | 7/1998 |
| WO | WO 92/07076 A1 | 4/1992 |
| WO | WO 92/13095 A1 | 8/1992 |

OTHER PUBLICATIONS

Ngo et al., 1994, The Protein Folding Problem and Tertiary Structure Prediction, pp. 492-495.*

Wells, Aditivity of Mutational Effects in Proteins, 1990, Biochemistry, vol. 26, No. 37, pp. 8509-8517.*

Adam-Klages S, et al, "FAN, a novel WD-repeat protein, couples the p55 TNF-receptor to neutral sphingomyelinase." Cell. 1996 Sep. 20:86(6):937-47.

Adolf GR, and Fruhbais B, "Monoclonal antibodies to soluble human TNF receptor (TNF binding protein) enhance its ability to block TNF toxicity." Cytokine. May;4(3):180-4 (1992).

Banner DW, et al., "Crystal structure of the soluble human 55 kd TNF receptor-human TNF beta complex: Implications for TNF receptor activation." Cell. May 7;73(3):431-45 (1993).

Beutler B, et al., "Identity of tumour necrosis factor and the macrophage-secreted factor cachectin." Nature. Aug. 8-14;316(6028):552-4 (1985).

Brakebusch C, et al., "Cytoplasmic truncation of the p55 tumour necrosis factor (TNF) receptor aboloshes signalling, but not induced shedding of the receptor," EMBO J. Mar.;11(3):943-50 (1992).

Carswell EA, et al., "An endotoxin-induced serum factor that causes necrosis of tumors." Proc. Natl Acad Sci U S A. Sep.;72(9):3666-70 (1975).

Christen U, et al, "Immune response to a recombinant human TNFR55-IgG1 fusion protein: auto-antibodies in rheumatold arthritis (RA) and multiple sclerosis (MS) patients have neither neutralizing nor agonist activities," Hum Immunol. Sep.;60(9):774-90 (1999).

Corcoran AE, et al., "Characterization of ligand binding by the human p55 tumour-necrosis-factor receptor. Involvement of individual cysteine-rich repeats." Eur J Biochem. Aug. 1;223(3):831-40 (1994).

(Continued)

*Primary Examiner*—Christine J. Saoud
*Assistant Examiner*—Jegatheesan Seharaseyon
(74) *Attorney, Agent, or Firm*—Dorsey & Whitney; Robin M. Silva; Timothy A. Worrall

(57) ABSTRACT

The invention relates to novel proteins with TNF-receptor antagonist activity and nucleic acids encoding these proteins. The invention further relates to TNF-receptor proteins with reduced immunogenicity and the use of these novel proteins in the treatment of TNF related disorders.

19 Claims, 14 Drawing Sheets

OTHER PUBLICATIONS

Eck MJ, et al., "The structure of human lymphotoxin (tumor necrosis factor-beta) at 1.9-A resolution." J Biol Chem. Feb. 5;267(4):2119-22 (1992).

Edwards CK 3rd. "PEGylated recombinant human soluble tumour necrosis factor receptor type 1 (r-Hu-sTNF-Rl): novel high affinity TNF receptor designed for chronic inflammatory diseases." Ann Rheum Dis. Nov.;58 Suppl 1:173-81 (1999).

Engelmann H, et al., "Two tumor necrosis factor-binding proteins purified from human urine. Evidence for immunological cross-reactivity with cell surface tumor necrosis factor receptors." J Biol Chem, Jan. 25;265(3):1531-6 (1990).

Espevik T, and Nissen-Meyer J. "A highly sensitive cell line, WEHI 164 clone 13, for measuring cytotoxic factor/tumor necrosis factor from human monocytes," J Immunol Methods. Dec. 4;95(1):99-105 (1986).

Grell M, "The transmembrane form of tumor necrosis factor is the prime activating ligand of the 80 kDa tumor necrosis factor receptor." Cell. Dec. 1;83(5):793-802 (1995).

Haak-Frendscho M, et al., "Inhibition of TNF by a TNF receptor immunoadhesin. Comparison to an anti-TNF monoclonal antibody." J Immunol. Feb. 1;152(3):1347-53 (1994).

Hakoshima T, and Tomita K. "Crystallization and preliminary X-ray investigation reveals that tumor necrosis factor is a compact trimer furnished with 3-fold symmetry." J Mol Biol. May 20;201(2):455-7 (1988).

Headon DJ, and Overbeek PA. "Involvement of a novel Tnf receptor homologue in hair follicle induction." Nat Genet. Aug.;22(4):370-4. (1999).

Jones EY, et al., "Structure of tumour necrosis factor." Nature. Mar. 16;338(6212):225-8 (1989).

Kim H, et al., "Receptor activator of $NF_{-K}B$ recruits multiple TRAF family adaptors and activates c-Jun N-terminal kinase." FEBS Lett. Dec. 7;443:297-302 (1999).

Kim I, "Molecular cloning and characterization of a novel angiopoietin family protein, angiopoietin-3." FEBS Lett. Jan. 29;443(3):353-6 (1999).

Loetscher H, et al., "Molecular cloning and expression of the human 55 kd tumor necrosis factor receptor." Cell. Apr. 20;61(2):351-9 (1990).

Loetscher H, et al., "Purification and partial amino acid sequence analysis of two distinct tumor necrosis factor receptors from HL60 cells." J Biol Chem. Nov. 25;265(33):20131-8 (1990).

Loetscher H, et al., "Recombinant 55-kDa tumor necrosis factor (TNF) receptor. Stoichiometry of binding to TNF alpha and TNF beta and inhibition of TNF activity." J Biol Chem. Sep. 25;266(27):18324-9 (1991).

Moreland LW. "Inhibitors of tumor necrosis factor: new treatment options for rheumatoid arthritis." Cleve Clin J Med. Jun.;66(6):367-74 (1999).

Naismith JH, et al., "Crystallographic Evidence for Dimerization of Unliganded Tumor Necrosis Factor Receptor." J Biol Chem. Jun. 2;270(2):13303-13307 (1995).

Naismith JH, and Sprang SR. "Modularity in the TNF-receptor family," Trends Biochem Sci. Feb.;23(2):74-9 (1998).

Naismith JH, et al., "Structures of the extracellular domain of the type 1 tumor necrosis factor receptor." Structure. Nov. 15;4(11):1241-62 (1996).

Old LJ. "Tumor necrosis factor (TNF)." Science. Nov. 8;230(4726):630-2 (1985).

Olsson I, et al., "Isolation and characterization of a tumor necrosis factor binding protein from urine." Eur J Haematol. Mar.;42(3):270-5 (1989).

Paquot N, "No increased insulin sensitivity after a single intravenous administration of a recombinant human tumor necrosis factor receptor: Fc fusion protein in obese insulin-resistant patients." J Clin Endocrinol Metab. Mar.;85(3):1316-9 (2000).

Park YC, "Structural basis for self-association and receptor recognition of human TRAF2." Nature. Apr. 8;398(6727):533-8 (1999).

Rodseth LE, et al., "Two crystal forms of the extracellular domain of type 1 tumor necrosis factor receptor." J Mol Biol. Jun. 3;239(2):332-5 (1994).

Scallon BJ, et al., "Functional comparisons of different tumour necrosis factor receptor/IgG fusion proteins." Cytokine. Nov. ;7(8):759-70 (1995).

Schall TJ, et al., "Molecular cloning and expression of a receptor for human tumor necrosis factor." Cell. Apr. 20;61(2):361-70 (1990).

Seckinger P, et al., "Tumor necrosis factor inhibitor: purification, NH2-terminal amino acid sequence and evidence for anti-inflammatory and immunomodulatory activities." Eur J Immunol. May;20(5):1167-74 (1990).

Smith CA, et al., "A receptor for tumor necrosis factor defines an unusual family of cellular and viral proteins." Science. May 25;248(4958):1019-23 (1990).

Takasaki W, "Structure-based design and characterization of exocyclic peptidomimetics that inhibit TNF alpha binding to its receptor." Nat Biotechnol. Nov.;15(12):1266-70 (1997).

Tartaglia LA, and Goeddel DV. "Tumor necrosis factor receptor signaling. A dominant negative mutation suppresses the activation of the 55-kDa tumor necrosis factor receptor." J Biol Chem. Mar. 5;267(7):4304-7 (1992).

Tartaglia LA, et al., "A novel domain within the 55 kd TNF receptor signals cell death." Cell. Sep. 10;74(5):845-53 (1993).

Tartaglia LA, et al., "The two different receptors for tumor necrosis factor mediate distinct cellular responses." Proc Natl Acad Sci U S A. Oct. 15;88(20):9292-6 (1991).

Tuma R, et al., "Solution conformation of the extracellular domain of the human tumor necrosis factor receptor probed by Raman and UV-resonance Raman spectroscopy: structural effects of an engineered PEG linker." Biochemistry, Nov. 21;34(46):15150-6 (1995).

Vandevoorde V, et al., "Induced expression of trimerized intracellular domains of the human tumor necrosis factor (TNF) p55 receptor elicits TNF effects." J Cell Biol. Jun. 30;137(7):1627-38 (1997).

Weiss T, et al., "Enhancement of TNF receptor p60-mediated cytotoxicity by TNF receptor p80: requirement of the TNF receptor-associated factor-2 binding site." J Immunol. Mar. 1;158(5):2398-404 (1997).

Ye H, and Wu H. "Thermodynamic characterization of the interaction between TRAF2 and tumor necrosis factor receptor peptides by isothermal titration calorimetry." Proc Natl Acad Sci U S A. Aug. 1;97(16):8961-6 (2000).

* cited by examiner

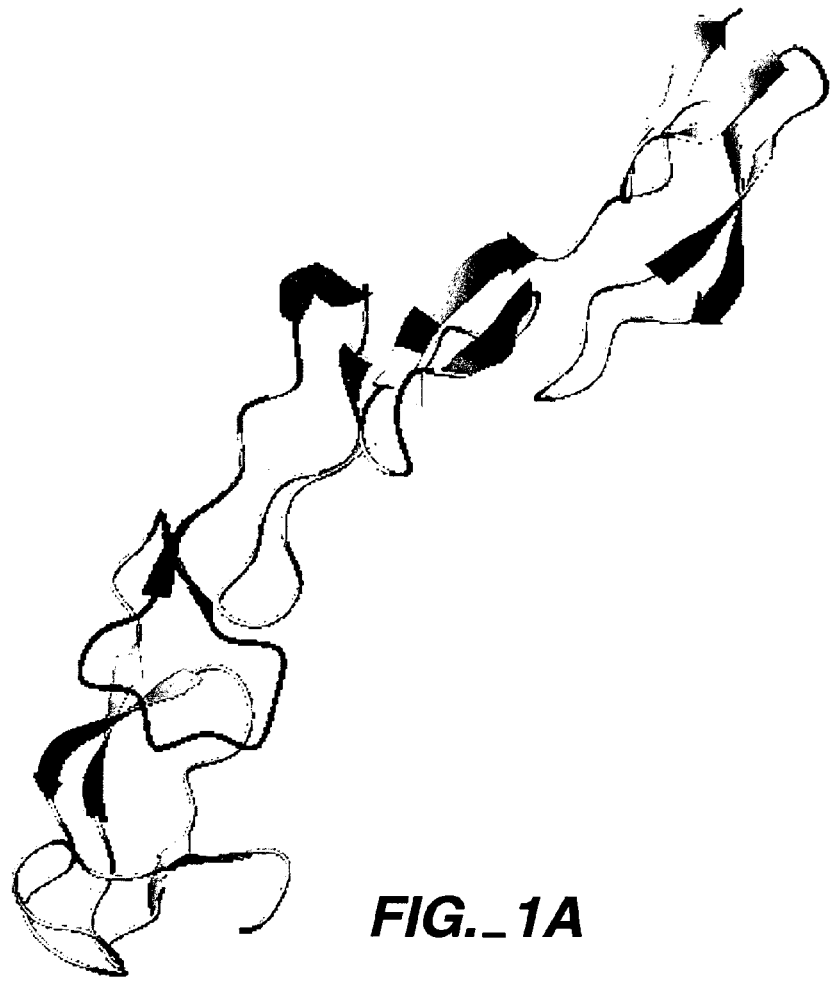
FIG._1A
-29                          -1 15
MGLSTVPDLLLPLVLLELLVGIYPSGVIGCPQGKYIHPQNNSICCTKCHKGTYLYNDC
PGPGQDTDCRECESGSFTASENHLRHCLSCSKCRKEMGQVEISSCTVDRDTVCGCRK
NQYRHYWSENLFQCFNCSLCLNGTVHLSCQEKQNTVCT<u>DYKDHDGDYKDHDIDYK</u>
<u>DDDDK</u>
FIG._1B

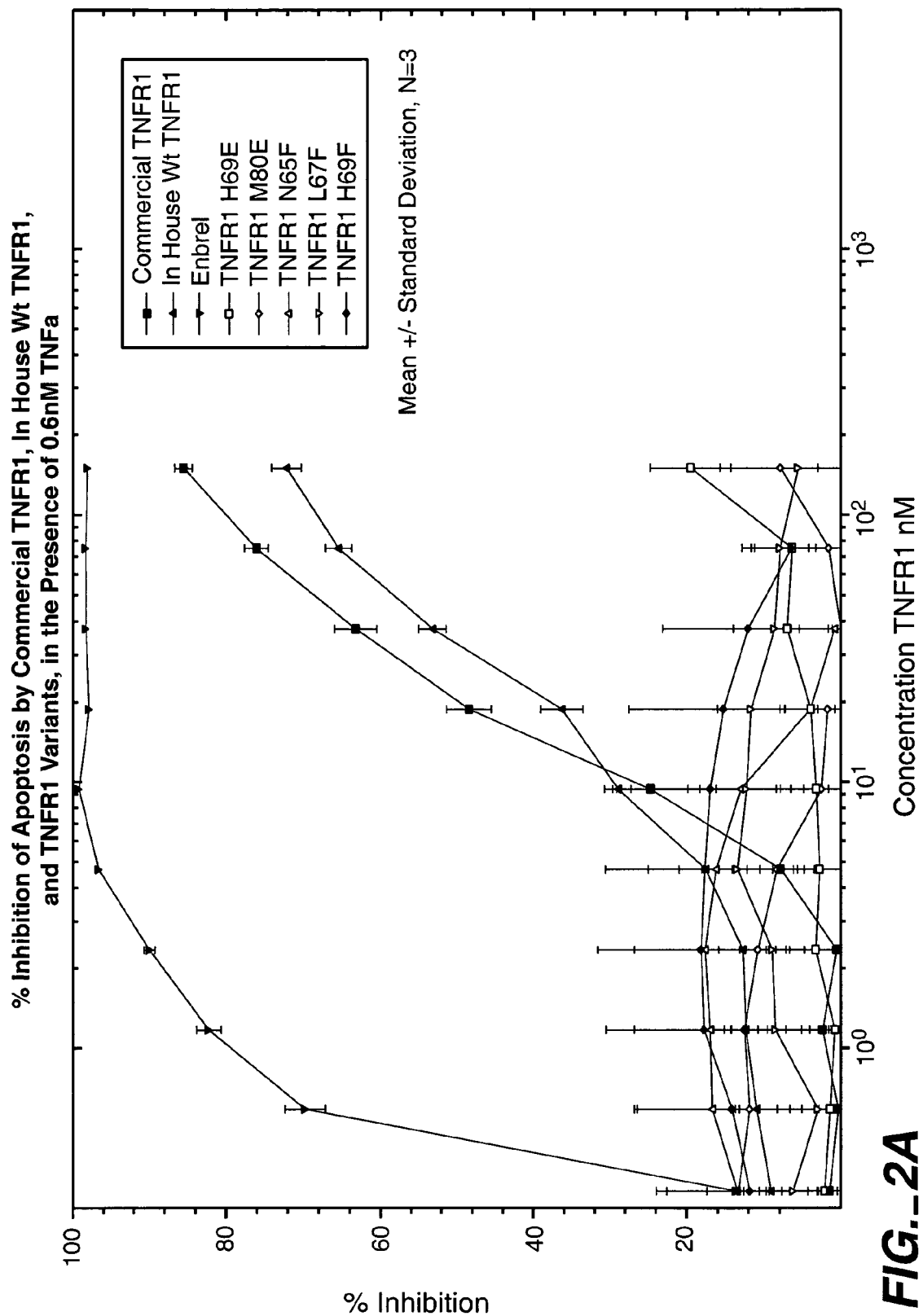
FIG._2A

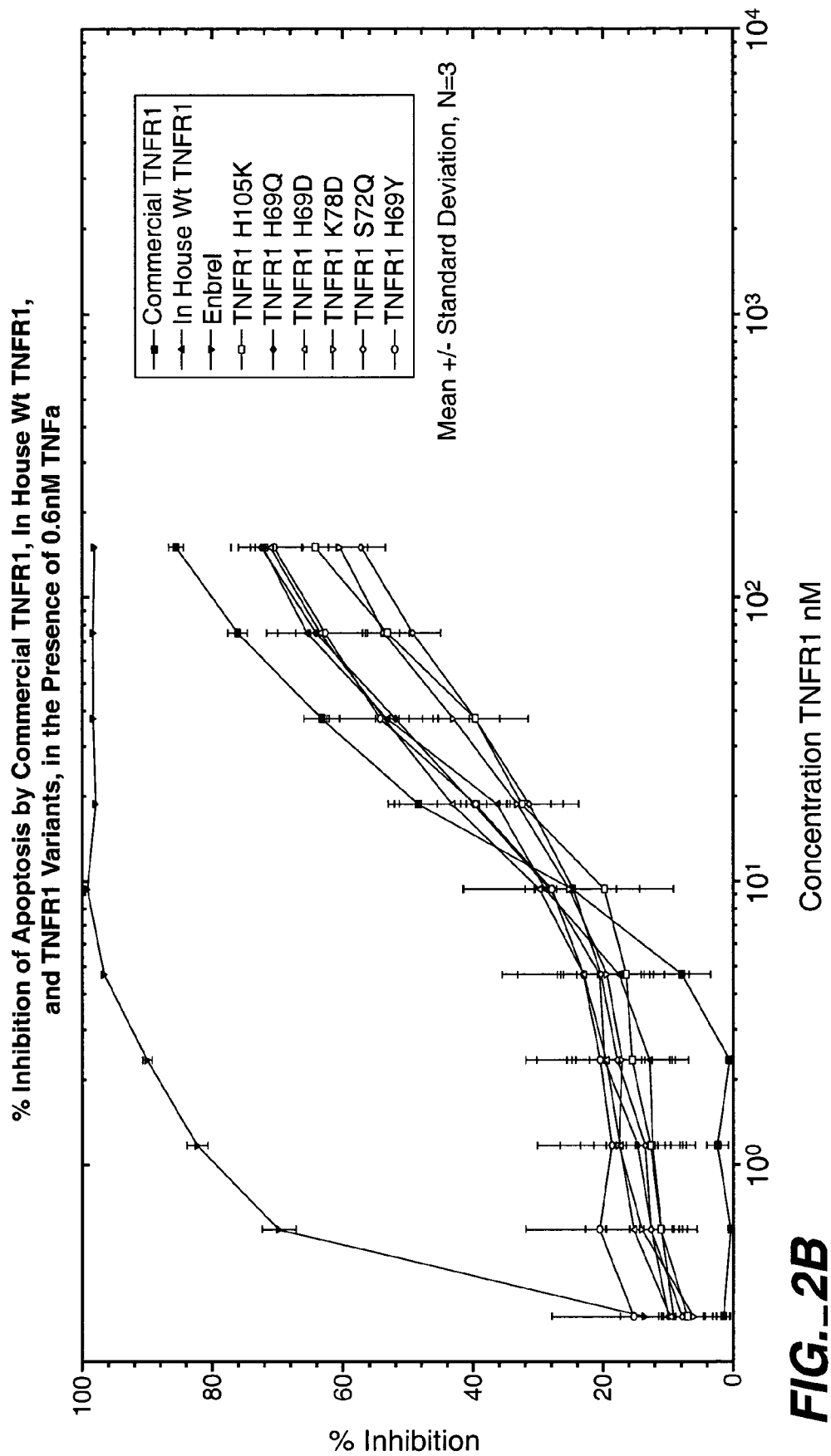
FIG._2B

% Inhibition of Apoptosis by Commercial TNFR1, In House Wt TNFR1, and TNFR1 Variants, in the Presence of 0.6nM TNFa

- Commercial TNFR1
- In House Wt TNFR1
- Enbrel
- TNFR1 H66F
- TNFR1 H69A
- TNFR1 K75R Mean +/- Standard Deviation, N=3

FIG._2C

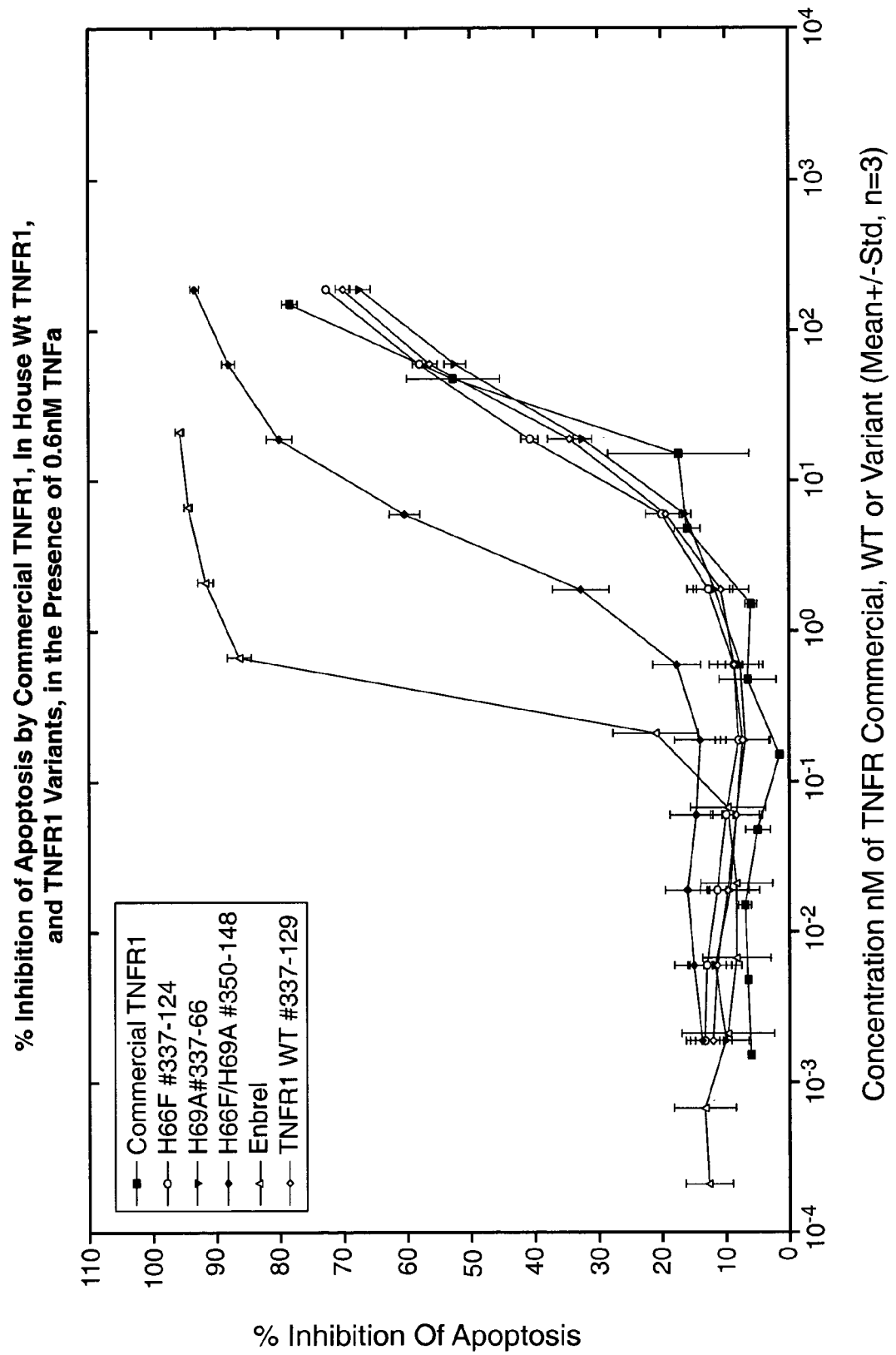
FIG._2D

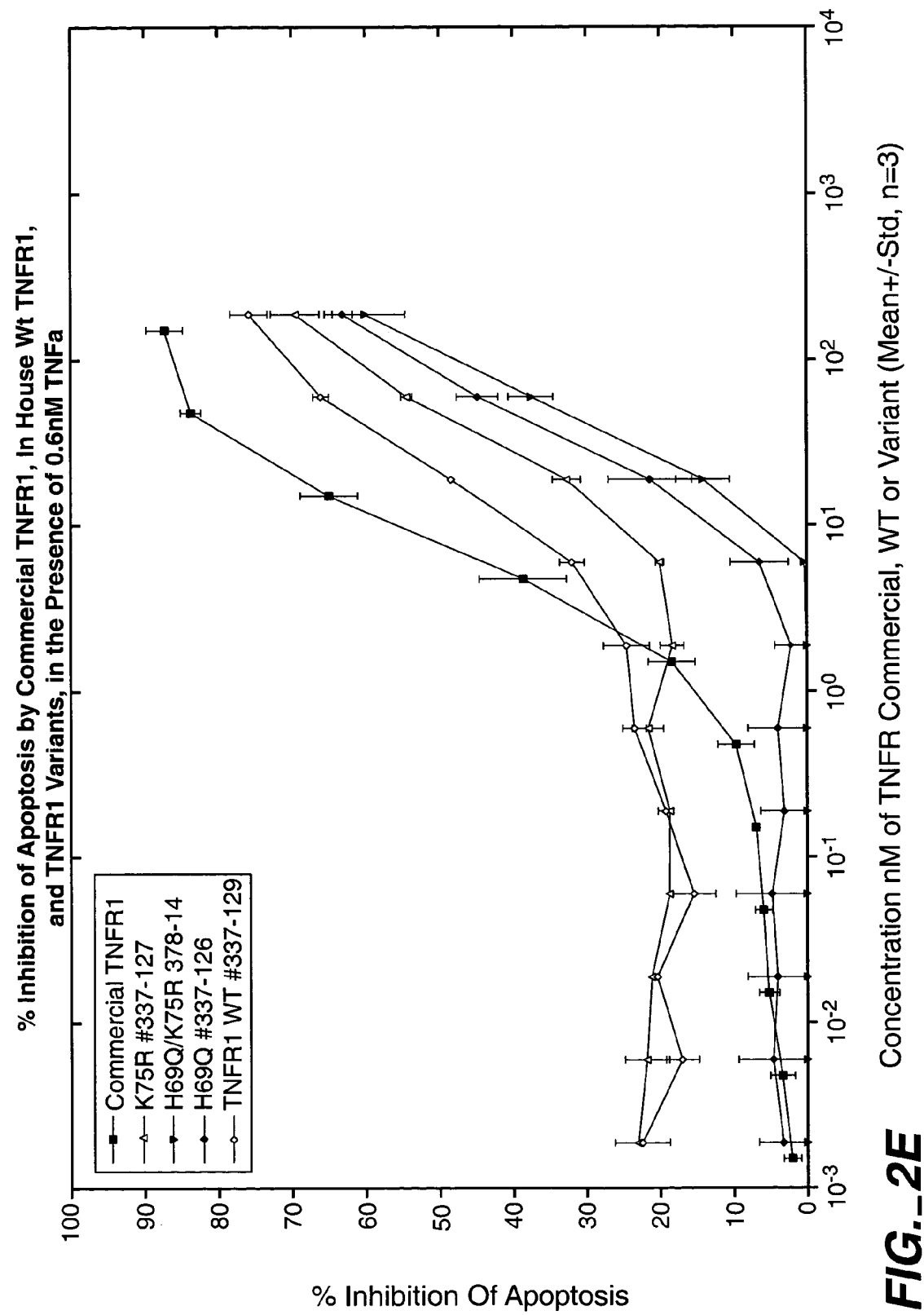
FIG._2E

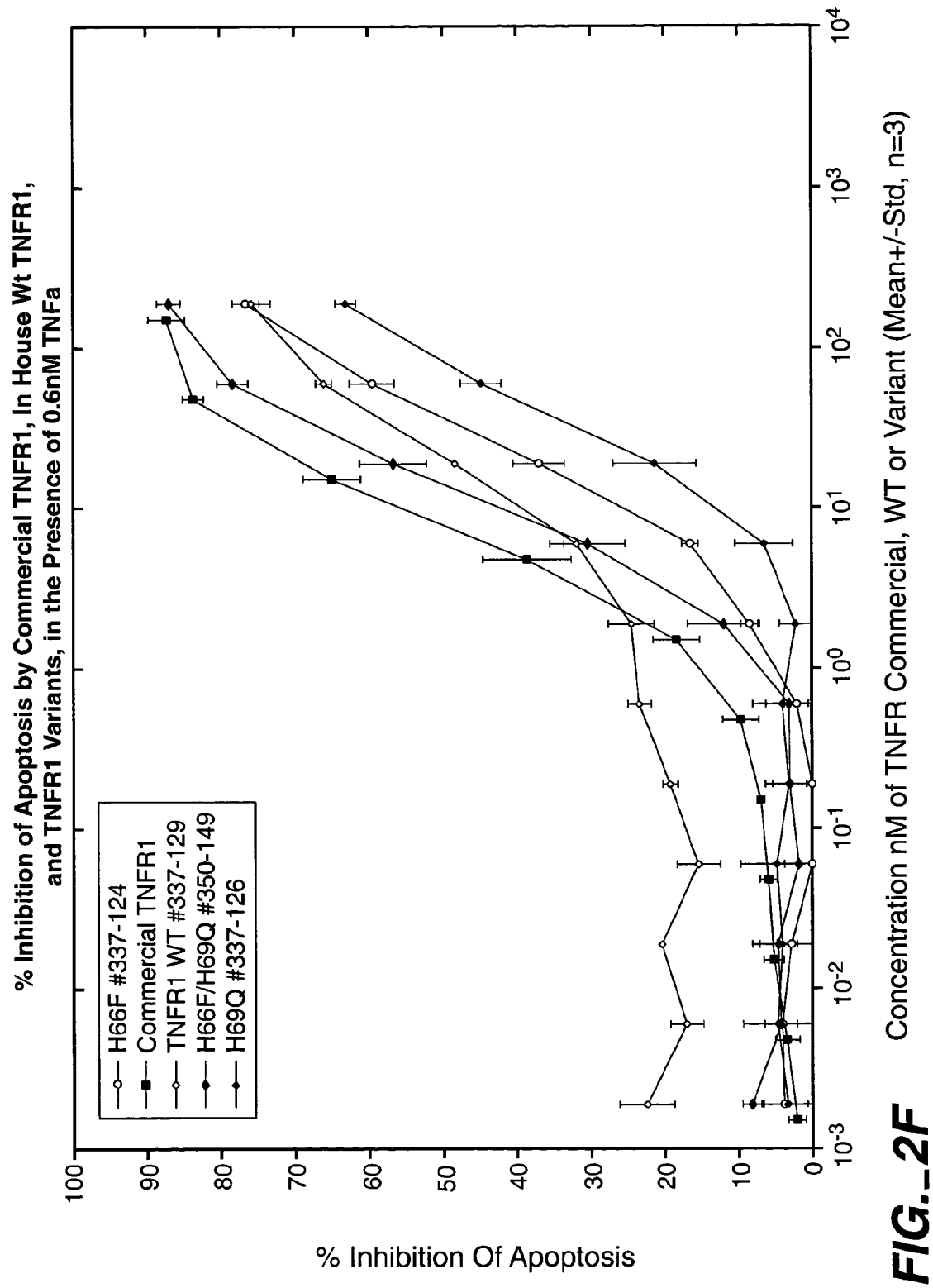
FIG._2F

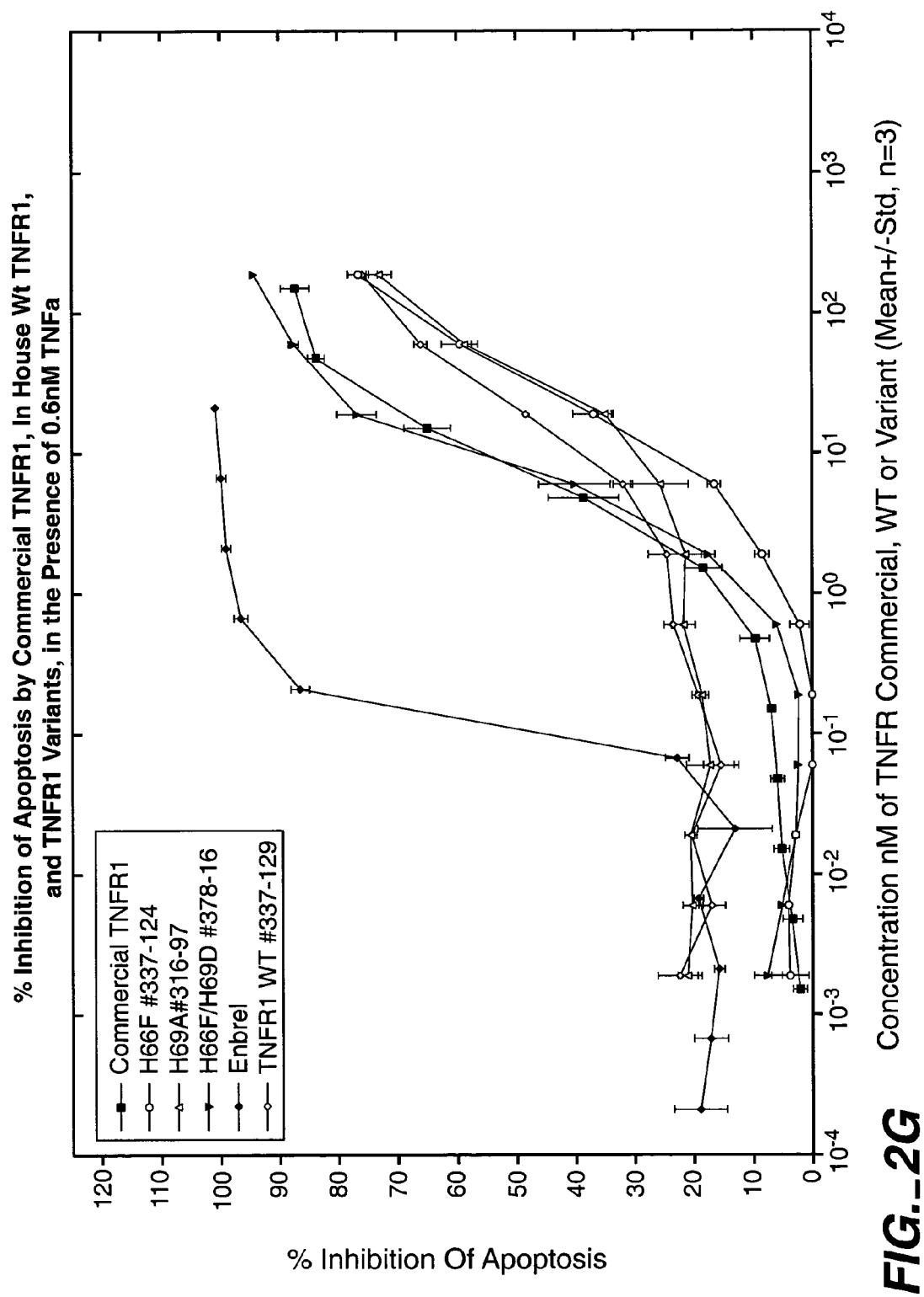
FIG._2G

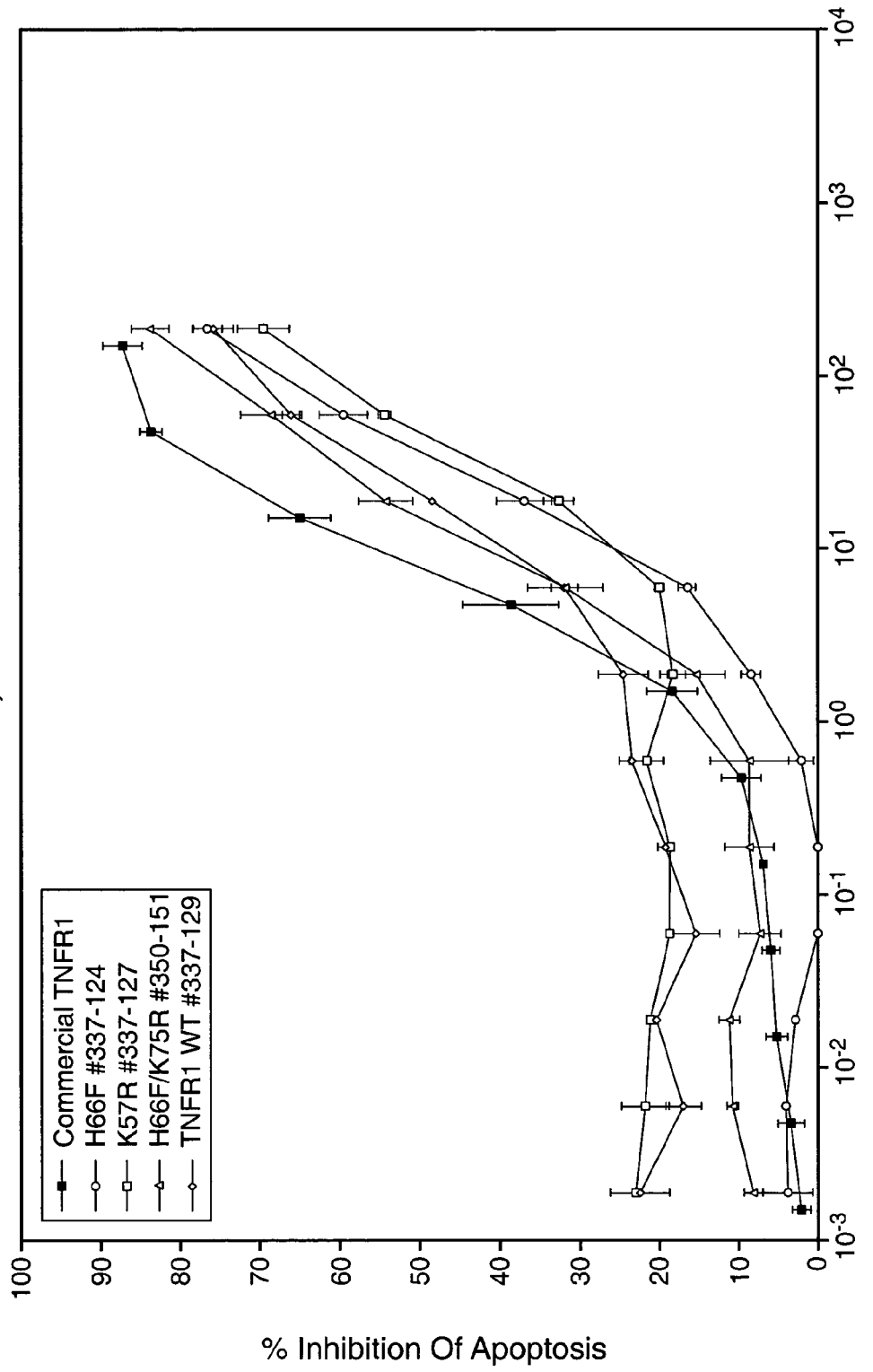
FIG._2H

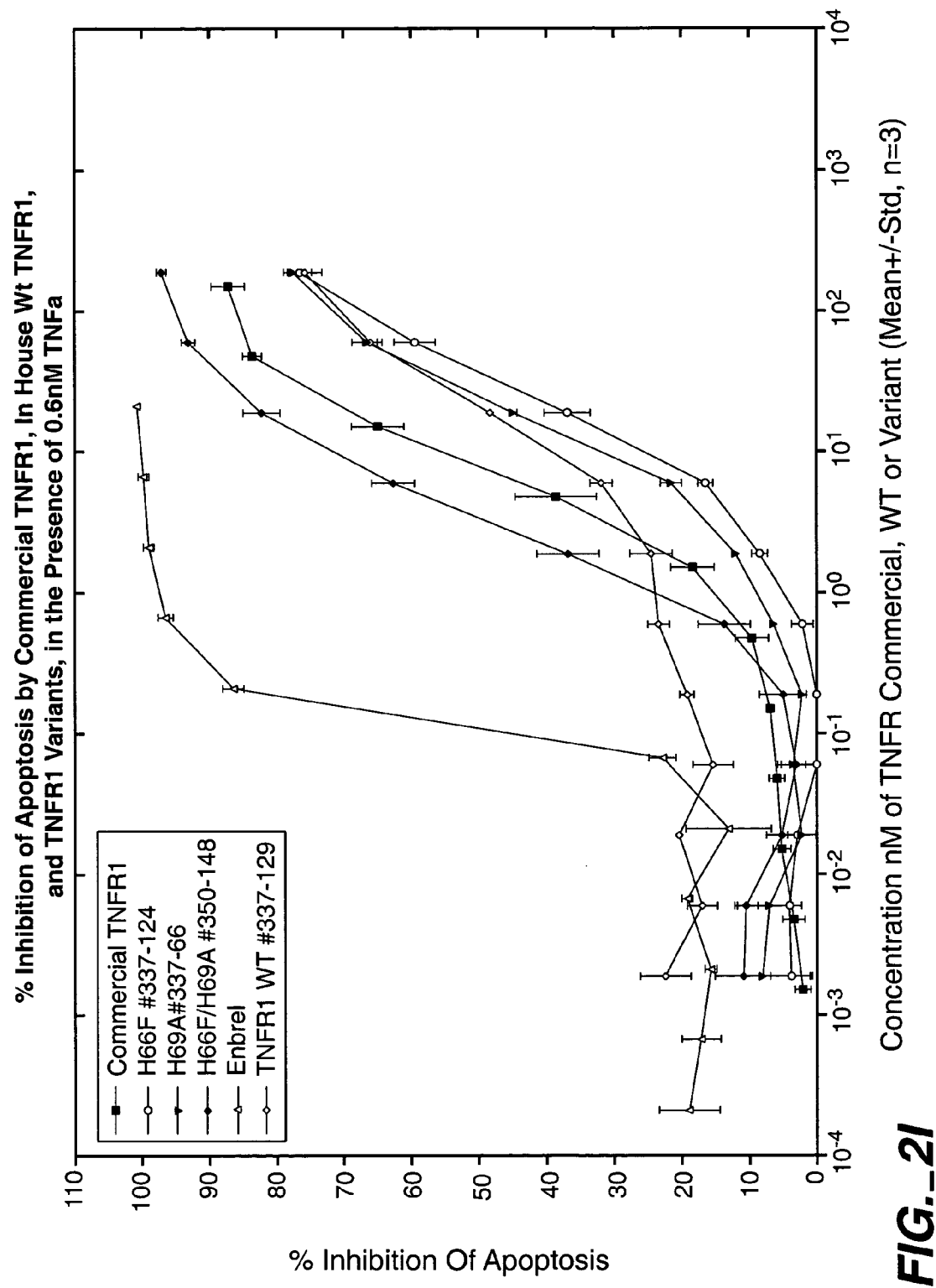
FIG._21

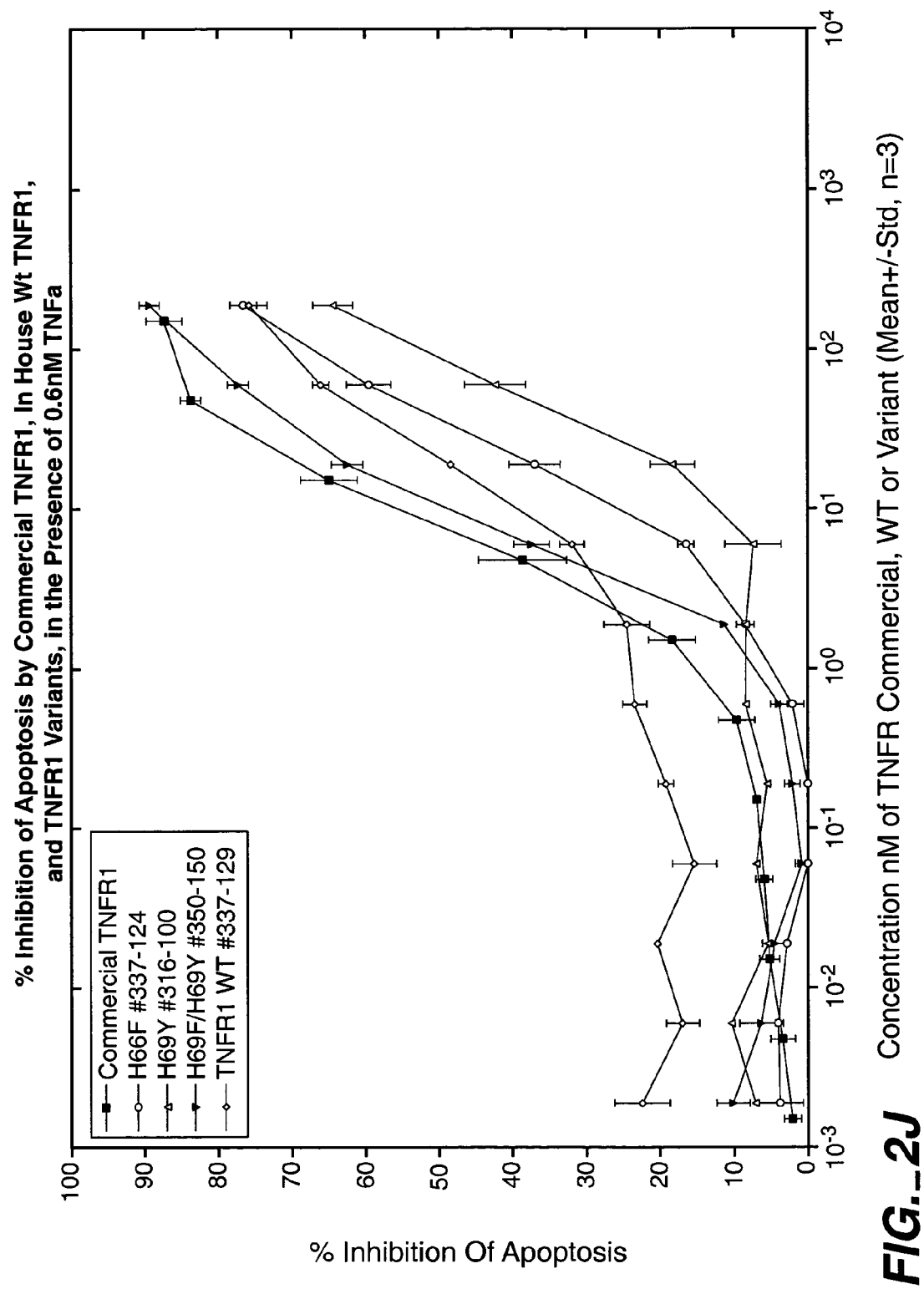
FIG._2J

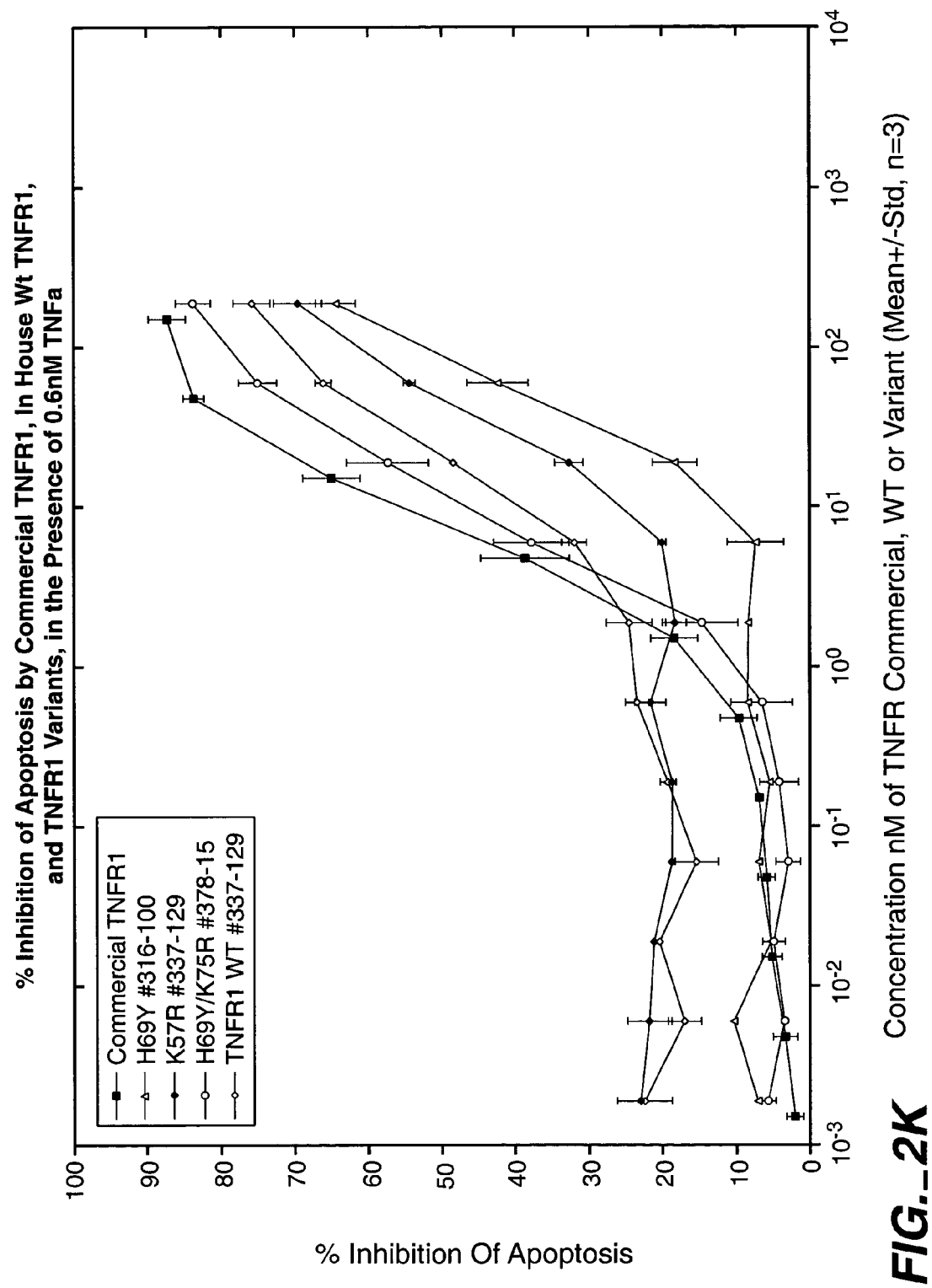
FIG._2K

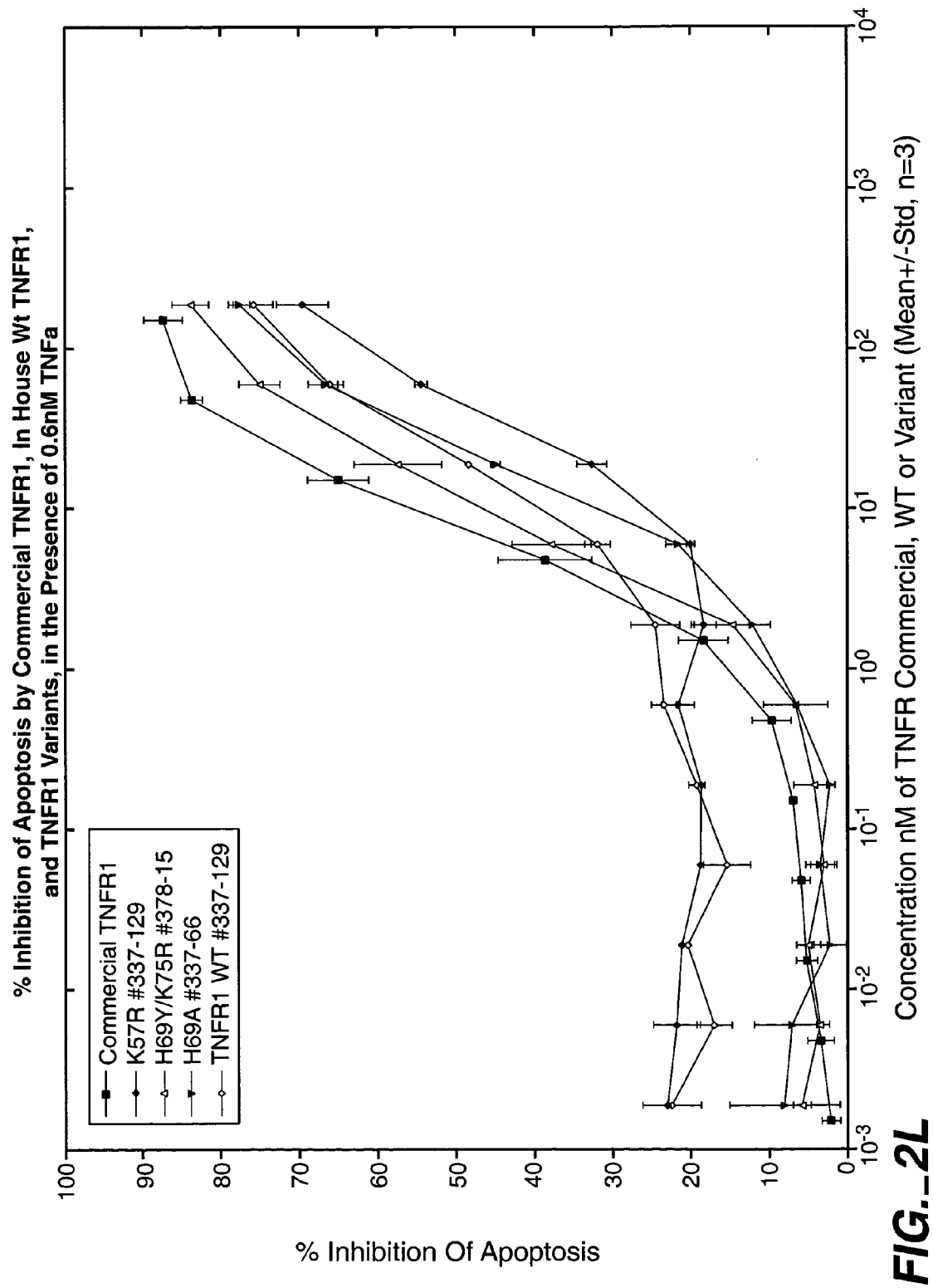
FIG._2L

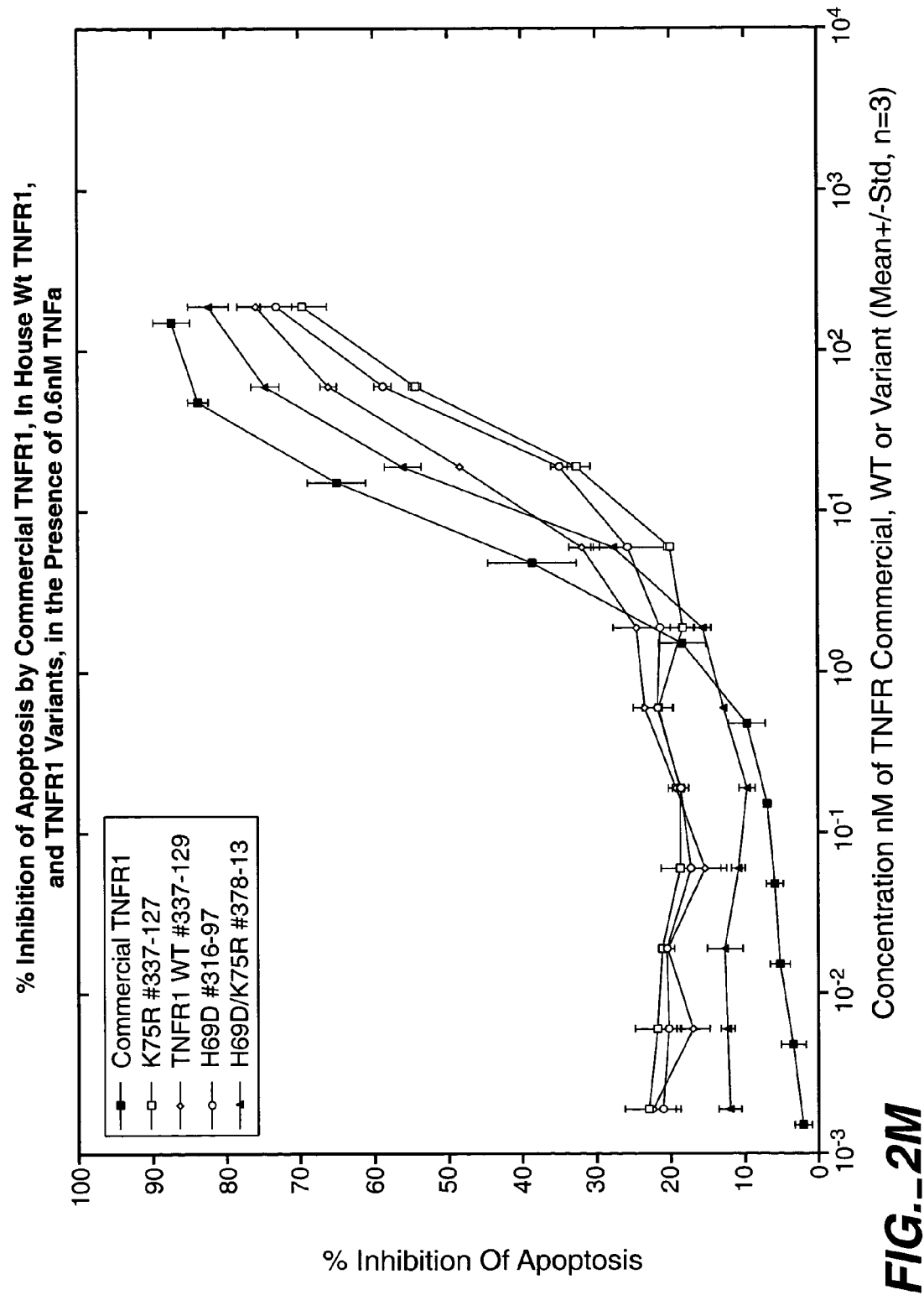
FIG._2M

PROTEIN BASED TUMOR NECROSIS FACTOR-RECEPTOR VARIANTS FOR THE TREATMENT OF TNF RELATED DISORDERS

This application claims the benefit of the filing date of U.S. Ser. No. 60/345,772, filed Jan. 4, 2002 and U.S. Ser. No. 60/415,545, filed Oct. 1, 2002, and is a continuation in part of U.S. Ser. No. 10/262,630, filed Sep. 30, 2002; U.S. Ser. No. 09/981,289, filed Oct. 15, 2001 now U.S. Pat. No. 7,101,974; U.S. Ser. No. 09/945,150, filed Aug. 31, 2001, now abandoned; and U.S. Ser. No. 09/798,789, filed Mar. 2, 2001 now U.S. Pat. No. 7,056,695, which claims the benefit of the filing date of U.S. Ser. No. 60/186,427, filed Mar. 2, 2000.

FIELD OF THE INVENTION

The invention relates to novel proteins with TNF-receptor antagonist activity and nucleic acids encoding these proteins. The invention further relates to novel TNF-receptor proteins with reduced immunogenicity and the use of these novel proteins in the treatment of TNF related disorders, such as autoimmune and inflammatory conditions.

BACKGROUND OF THE INVENTION

Tumor Necrosis Factor (TNF) was originally discovered as a naturally occurring secreted protein with potent cytotoxic activity on tumor cells (Carswell, E. A., et al. (1075) PNAS, 72:3666–3670; Old, L. J. (1985) Science, 230: 630–632; and Beutler, B. et al. (1985) Nature, 316:552–554). TNF exerts its biological effects through interaction with high-affinity cell surface receptors which trigger specific cellular responses. Two distinct membrane TNF-receptors have been cloned and characterized. These are a 55 kDa species, designated p55 TNF-R1 and a 75 kDa species designated p75 TNF-R2 (Loetscher, H. Y. et al. (1990), Cell 61:351–360; Schall, T. J. et al. (1990), Cell 61:361; Smith, C. A. et al. (1990), Science 248:1019; Corcoran, A. E., et al., (1994) Eur. J. Biochem., 223: 831–840).

Expression of TNFR1 can be demonstrated on almost every mammalian cell while TNFR2 expression is largely limited to cells of the immune system and endothelial cells. Each receptor elicits a distinct signal: the intracellular portion of TNFR1 contains a "death domain" which initiates the apoptotic pathway and NFkB activation when triggered (Tartaglia, L. A. et al. (1991) PNAS 88:9292–10296; Tartaglia, L. A. et al. (1993), Cell 74: 845–853). The role of TNFR2 is less clear as it has no direct apoptotic signaling but can activate NFkB, resulting in transcriptional activation of genes required for the inflammatory and immune response.

The two TNF receptors exhibit 28% similarity at the amino acid level. This is confined to the extracellular domain and consists of four repeating cysteine-rich motifs, each of approximately 40 amino acids. Each motif contains four to six cysteines in conserved positions. Dayhoff analysis shows the greatest intersubunit similarity among the first three repeats which contains the ligand binding section. This characteristic structure is shared with a number of other receptors and cell surface molecules, which comprise the TNF-R/nerve growth factor receptor superfamily (Corcoran, A. E., et al., (1994) Eur. J. Biochem., 223:831–840).

Crystallographic studies of TNF-alpha and the structurally related cytokine, lymphotoxin or TNF-beta (LT) have shown that both cytokines exist as homotrimers, with subunits packed edge to edge in a threefold symmetry (Hakoshima, T. and Tomita, K. (1988) J. Mol. Biol. 201:455–457; Jones, E. Y. et al. (1989) Nature 338:225–228; Eck, M. J. et al. (1992) J. Biol. Chem. 267:2119–2122).

TNF signaling is initiated by receptor clustering, either by the trivalent ligand TNF or by cross-linking monoclonal antibodies (Vandevoorde, V., et al., (1997) J. Cell Biol., 137:1627–1638). Structurally, neither TNF or LT reflect the repeating pattern of the their receptors. Each monomer is cone shaped and contains two hydrophilic loops on opposite sides of the base of the cone. The crystal structure determination of a p55 soluble TNF-R/LT complex has confirmed the hypothesis that loops from adjacent monomers join together to form a groove between monomers and that TNF-R binds in these grooves (Banner, E. W. et al. (1993) Cell, 73:431–435).

TNF plays an important role in regulating inflammation, cellular immune response, and host defense. Conversely in diseases such as rheumatoid arthritis, osteoarthritis, psoriasis, Crohn's disease, inflammatory bowel disease and other chronic disorders of the immune system, excessive levels of TNF play a role in the pathophysiology. Indeed, blocking TNF can halt disease progression and has led to the search for antagonists of TNF.

Several strategies at blocking TNF signaling can be employed: inhibiting TNF biosynthesis, inhibiting TNF secretion or shedding, or blocking the interaction of TNF with its receptors. A natural mechanism to down regulate TNF exists whereby the extra-cellular portion of the TNF receptor is enzymatically cleaved resulting in a freely circulating TNF binding protein or "soluble receptor" which retains its affinity for TNF but neutralizes its ability to signal through its cell surface receptor (Engelmann, H. et al. (1990) J. Biol. Chem. 265:1531–1536; Olsson, et al. (1989) Eur. J. Haematol. 42:270–275; Seckinger et al. (1990) Eur. J. Immunol. 20: 1167–1174). In cases such as autoimmune disease and chronic inflammation excessively high levels of TNF overwhelms the ability to self-regulate.

The therapeutic use of soluble TNF receptors has been proven to be an effective way to block TNF signaling. For example, ENBREL®, a soluble bivalent form of TNFR2 fused to a human immunoglobulin fragment (Fc) is used for the treatment of rheumatoid arthritis and psoriasis. Soluble TNFR1-Fc has also been shown to effectively block TNF-mediated effects in animal models but has not been approved for use in humans (Lenercept) due to immunogenicity concerns (Christen, U. et al Human Immunol. 60:774–790, 1999).

While protein engineering techniques resulting in loss-of-function (i.e. random mutagenesis) have defined regions of TNF-TNFR interaction, no successful gain-of-function has been engineered into soluble TNFR. That is, there are no known designs of a less immunogenic soluble TNFR1 protein with an enhanced ability (relative to wild-type) to block TNF-mediated effects.

Therefore, a need still exists to develop more potent, less immunogenic TNF-receptor antagonists for use as therapeutic agents. Accordingly, it is an object of the invention to provide proteins with TNF-receptor antagonist activity and nucleic acids encoding these proteins for the treatment of TNF related disorders.

SUMMARY OF THE INVENTION

In accordance with the objects outlined above, the present invention provides non-naturally occurring variant TNF-receptor proteins (e.g. proteins not found in nature) comprising amino acid sequences with at least one non-conservative amino acid change compared to the wild type TNF-receptor proteins.

Preferred embodiments utilize variant TNF-receptor proteins that interact with the wild type TNF to inactivate receptor signaling.

Other embodiments include TNF-receptor proteins that have enhanced antagonistic properties as compared to wild type TNF-receptors.

Preferably, variant TNF-receptor proteins with 1, 2, 3, 4, and 5 amino acid changes are used as compared to wild type TNF-receptor protein. In a preferred embodiment, at least one of these changes is non-conservative. More preferably, these changes are selected from positions 65, 66, 67, 69, 72, 75, 77, 78, 79, 80, 105, 107, 108, 111 and 113.

In an additional aspect, the non-naturally occurring variant TNF-receptor proteins have substitutions selected from the group of substitutions consisting of N65E, N65F, N65V, H66F, H66K, H66R, H66W, L67F, L67K, H69A, H69D, H69E, H69F, H69K, H69R, H69T, H69Y, H69Q, S72A, S72L, S72G, S72N, S72R, S72O, K75Q, K75R, R77D, R77K, R77L, R77Q, R77V, K78D, K78R, E79A, E79H, E79K, E79S, E79T, E79W, M80A, M80D, M80E, M80L, H105K, W107A, W107B, W107D, W107E, W107F, W107K, W107Q, W107T, S108H, S108T, S108W, L111E, L111K, L111Q, L111R, Q113F, Q1131, Q113K, Q113R, and Q113Y and combinations thereof.

Another aspect provides a non-naturally occurring TNF-receptor molecule that has reduced immunogenicity. Preferred variants for reduced immunogenicity include changes at positions 66, 69 and 75. More specifically, the TNF-receptor variants that are preferred include H69A, H69D, H69Q, K75R and H66F and H69D. The variant H69D and the double variant H69D+H$_{66}$F are most preferred.

In a further embodiment, the TNF-receptor molecule may be chemically modified. In addition, portions of the N- or C-termini may deleted. In an additional aspect, the two or more receptor interaction domains of the naturally occurring TNF-receptor or the TNF-receptor variant proteins may be covalently linked by a linker peptide or by other means.

In a further aspect, the invention provides recombinant nucleic acids encoding the non-naturally occurring variant TNF-receptor proteins, expression vectors, and host cells.

In an additional aspect, the invention provides methods of producing a non-naturally occurring variant TNF-receptor protein comprising culturing the host cell of the invention under conditions suitable for expression of the nucleic acid. In a further aspect, the invention provides pharmaceutical compositions comprising a variant TNF-receptor protein of the invention and a pharmaceutical carrier.

In a further aspect, the invention provides methods for treating an TNF related disorder comprising administering a variant TNF-receptor protein of the invention to a patient in need of said treatment.

BRIEF DESCRIPTION OF THE DRAWINGS

FIG. 1A depicts the structure of the p55 TNF-R extracellular domain. The darker appearing regions represent residues required for contact with TNF-receptor. FIG. 1B depicts the sequence of the p55 TNF-R extra-cellular domain used as the starting structure in the present invention—a flag tagged truncated soluble TNF-R. The sequence depicted in FIG. 1B differs from the wild type p55TNF-R sequence in that the ligand binding region, which is composed of the first 3 cysteine rich domains (the 4$^{th}$ domain is omitted), is C-terminally fused to a flag sequence. The initiator methionine and the signal peptide are from wild-type gene (the signal peptide is deleted as well as the N-terminal sequence (IYPSGVIG)). As shown in FIG. 1B, a 14 amino acid deletion was engineered between residues −1 and 15 (L$_{VPHLGDREKRDSV}$). The initial leucine residue of this section corresponds to the first residue of the crystallized structure and is considered residue 1 for the TNF-R starting point molecule of the present invention.

FIGS. 2A–M are graphical representations of percent inhibition of apoptosis of TNF-induced capase-3 activity by TNFR1 variants of the present invention v. wild type TNFR1 (R&D Systems, Inc.).

DETAILED DESCRIPTION OF THE INVENTION

The present invention is directed to novel proteins and nucleic acids possessing TNF-receptor antagonist activity. The proteins may be preferably generated using PDA™ technology previously described in WO98/47089 and U.S. Ser. Nos. 09/058,459, 09/127,926, 60/104,612, 60/158,700, 09/419,351, 60/181,630, 60/186,904, 09/419,351, 09/782, 004 and 09/927,790, 60/347,772, and 10/218,102, all of which are expressly incorporated by reference in their entirety. In general, these applications describe a variety of computational modeling systems that allow the generation of extremely stable proteins. In this way, variants of TNF-R proteins are generated that act as antagonists for wild type TNF. Variant TNF-R proteins may be generated from wild type TNF-receptor, p55 TNF-R and p75 TNF-R proteins, with preferred embodiments including variant TNF-receptor proteins, more preferred is the p55 TNF-R.

Generally, there are a variety of computational methods that can be used to generate a library of primary variant sequences. In a preferred embodiment, sequence-based methods are used. Other models for assessing the relative energies of sequences with high precision include Warshel, *Computer Modeling of Chemical Reactions in Enzymes and Solutions*, Wiley & Sons, New York, (1991), as well as the models identified in U.S. Ser. No. 10/218,102, filed Aug. 12, 2002, all hereby expressly incorporated by reference. Similarly, molecular dynamics calculations can be used to computationally screen sequences by individually calculating mutant sequence scores and compiling a list.

In a preferred embodiment, residue pair potentials can be used to score sequences (Miyazawa et al., Macromolecules 18(3):534–552 (1985), expressly incorporated by reference) during computational screening.

In a preferred embodiment, sequence profile scores (Bowie et al., Science 253(5016):164–70 (1991), incorporated by reference) and/or potentials of mean force (Hendlich et al., J. Mol. Biol. 216(1):167–180 (1990), also incorporated by reference) may also be calculated to score sequences. These methods assess the match between a sequence and a 3-D protein structure and hence can act to screen for fidelity to the protein structure. By using different scoring functions to rank sequences, different regions of sequence space can be sampled in the computational screen.

Furthermore, scoring functions may be used to screen for sequences that would create metal or co-factor binding sites in the protein (Hellinga, Fold Des. 3(1): R1–8 (1998), hereby expressly incorporated by reference). Similarly, scoring functions may be used to screen for sequences that would create disulfide bonds in the protein. These potentials attempt to specifically modify a protein structure to introduce a new structural motif.

In a preferred embodiment, sequence and/or structural alignment programs may be used to generate the variant TNF-receptor proteins of the invention. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise.

The source of the sequences may vary widely, and include taking sequences from one or more of the known databases, including, but not limited to, SCOP (Hubbard, et al., Nucleic Acids Res 27(1):254–256. (1999)); PFAM (Bateman, et al., Nucleic Acids Res 27(1):260–262. (1999)); VAST (Gibrat, et al., Curr Opin Struct Biol 6(3):377–385. (1996)); CATH (Orengo, et al., Structure 5(8):1093–1108. (1997)); PhD Predictor (http://www.embl-heidelberg.de/predictprotein/predictprotein.html); Prosite (Hofmann, et al., Nucleic Acids Res 27(1):215–219. (1999)); PIR (http://www.mips.biochem.mpg.de/proj/protseqdb/); GenBank (http://www.ncbi.nlm.nih.gov/); PDB (www.rcsb.org) and BIND (Bader, et al., Nucleic Acids Res 29(1):242–245. (2001)).

In addition, sequences from these databases may be subjected to contiguous analysis or gene prediction; see Wheeler, et al., Nucleic Acids Res 28(1):10–14. (2000) and Burge and Karlin, J Mol Biol 268(1):78–94. (1997).

As is known in the art, there are a number of sequence alignment methodologies that may be used. For example, sequence homology based alignment methods may be used to create sequence alignments of proteins related to the target structure (Altschul et al., J. Mol. Biol. 215(3):403–410 (1990), Altschul et al., Nucleic Acids Res. 25:3389–3402 (1997), both incorporated by reference). These sequence alignments are then examined to determine the observed sequence variations. These sequence variations are tabulated to define a set of variant TNF-receptor proteins.

Sequence based alignments may be used in a variety of ways. For example, a number of related proteins may be aligned, as is known in the art, and the "variable" and "conserved" residues defined; that is, the residues that vary or remain identical between the family members can be defined. These results may be used to generate a probability table, as outlined below. Similarly, these sequence variations may be tabulated and a secondary library defined from them as defined below. Alternatively, the allowed sequence variations may be used to define the amino acids considered at each position during the computational screening. Another variation, is to bias the score for amino acids that occur in the sequence alignment, thereby increasing the likelihood that they are found during computational screening but still allowing consideration of other amino acids. This bias would result in a focused library of variant TNF-receptor proteins but would not eliminate from consideration amino acids not found in the alignment. In addition, a number of other types of bias may be introduced. For example, diversity may be forced; that is, a "conserved" residue is chosen and altered to force diversity on the protein and thus sample a greater portion of the sequence space. Alternatively, the positions of high variability between family members (i.e. low conservation) may be randomized, either using all or a subset of amino acids. Similarly, outlier residues, either positional outliers or side chain outliers, may be eliminated.

Similarly, structural alignment of structurally related proteins may be done to generate sequence alignments. There are a wide variety of such structural alignment programs known. See for example VAST from the NCBI (http://www.ncbi.nlm.nih.gov:80/Structure/VAST/vast.shtml); SSAP (Orengo and Taylor, Methods Enzymol 266(617–635 (1996)) SARF2 (Alexandrov, Protein Eng 9(9):727–732. (1996)) CE (Shindyalov and Bourne, Protein Eng 11(9):739–747. (1998)); (Orengo et al., Structure 5(8):1093–108 (1997); Dali (Holm et al., Nucleic Acid Res. 26(1):316–9 (1998), all of which are incorporated by reference). These sequence alignments may then be examined to determine the observed sequence variations. Libraries may be generated by predicting secondary structure from sequence, and then selecting sequences that are compatible with the predicted secondary structure. There are a number of secondary structure prediction methods such as helix-coil transition theory (Munoz and Serrano, Biopolymers 41:495,1997), neural networks, local structure alignment and others (e.g., see in Selbig et al., Bioinformatics 15:1039–46, 1999).

Similarly, as outlined above, other computational methods are known, including, but not limited to, sequence profiling [Bowie and Eisenberg, Science 253(5016):164–70, (1991)], rotamer library selections [Dahiyat and Mayo, Protein Sci. 5(5):895–903 (1996); Dahiyat and Mayo, Science 278(5335):82–7 (1997); Desjarlais and Handel, Protein Science 4:2006–2018 (1995); Harbury et al, Proc. Natl. Acad. Sci. U.S.A. 92(18):8408–8412 (1995); Kono et al., Proteins: Structure, Function and Genetics 19:244–255 (1994); Hellinga and Richards, Proc. Natl. Acad. Sci. U.S.A. 91:5803–5807 (1994)]; and residue pair potentials [Jones, Protein Science 3: 567–574, (1994)]; PROSA [Heindlich et al., J. Mol. Biol. 216:167–180 (1990)]; THREADER [Jones et al., Nature 358:86–89 (1992)], and other inverse folding methods such as those described by Simons et al. [Proteins, 34:535–543, (1999)], Levitt and Gerstein [Proc. Natl. Acad. Sci. U.S.A., 95:5913–5920, (1998)], Godzik and Skolnick [Proc. Natl. Acad. Sci. U.S.A., 89:12098–102, (1992)], Godzik et al. [J. Mol. Biol. 227:227–38, (1992)] and two profile methods [Gribskov et al. Proc. Natl. Acad. Sci. U.S.A. 84:4355–4358 (1987) and Fischer and Eisenberg, Protein Sci. 5:947–955 (1996), Rice and Eisenberg J. Mol. Biol. 267:1026–1038(1997)], all of which are expressly incorporated by reference.

In addition, other computational methods such as those described by Koehl and Levitt (J. Mol. Biol. 293:1161–1181 (1999); J. Mol. Biol. 293:1183–1193 (1999); expressly incorporated by reference) may be used to create a variant TNF-receptor library which may optionally then be used to generate a smaller secondary library for use in experimental screening for improved properties and function. In addition, there are computational methods based on force field calculations such as SCMF, see Delarue et al. Pac. Symp. Biocomput. 109–21 (1997); Koehl et al., J. Mol. Biol. 239:249–75 (1994); Koehl et al., Nat. Struct. Biol. 2:163–70 (1995); Koehl et al., Curr. Opin. Struct. Biol. 6:222–6 (1996); Koehl et al., J. Mol. Biol. 293:1183–93 (1999); Koehl et al., J. Mol. Biol. 293:1161–81 (1999); Lee J., Mol. Biol. 236:918–39 (1994); and Vasquez Biopolymers 36:53–70 (1995); all of which are expressly incorporated by reference. Other force field calculations that can be used to optimize the conformation of a sequence within a computational method, or to generate de novo optimized sequences as outlined herein include, but are not limited to, OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc. 110:1657ff (1988); Jorgensen et al., J. Am. Chem. Soc.112:4768ff (1990)]; UNRES (United Residue Forcefield; Liwo et al., Protein Science 2:1697–1714 (1993);

Liwo et al., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A. 96:5482–5485 (1999)]; ECEPP/3 [Liwo et al., J Protein Chem. 13(4):375–80 (1994)]; AMBER 1.1 force field (Weiner et al., J. Am. Chem. Soc. 106:765–784); AMBER 3.0 force field [U. C. Singh et al., Proc. Natl. Acad. Sci. U.S.A. 82:755–759 (1985)]; CHARMM and CHARMM22 (Brooks et al., J. Comp. Chem. 4:187–217); cvff3.0 [Dauber-Osguthorpe et al., Proteins: Structure, Function and Genetics, 4:31–47 (1988)]; cff91 (Maple et al., J. Comp. Chem. 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference. In fact, as is outlined below, these force field methods may be used to generate the variant TNF-receptor library directly; these methods may be used to generate a probability table from which an additional library is directly generated.

The PDA™ technology, viewed broadly, has three components that may be varied to alter the output (e.g. the primary library): the scoring functions used in the process; the filtering technique, and the sampling technique.

In a preferred embodiment, the scoring functions may be altered. In a preferred embodiment, the scoring functions outlined above may be biased or weighted in a variety of ways. For example, a bias towards or away from a reference sequence or family of sequences can be done; for example, a bias towards wild type or homologue residues may be used. Similarly, the entire protein or a fragment of it may be biased; for example, the active site may be biased towards wild type residues, or domain residues towards a particular desired physical property can be done. Furthermore, a bias towards or against increased energy can be generated. Additional scoring function biases include, but are not limited to applying electrostatic potential gradients or hydrophobicity gradients, adding a substrate or binding partner to the calculation, or biasing towards a desired charge or hydrophobicity.

In addition, in an alternative embodiment, there are a variety of additional scoring functions that may be used. Additional scoring functions include, but are not limited to torsional potentials, or residue pair potentials, or residue entropy potentials. Such additional scoring functions can be used alone, or as functions for processing the library after it is scored initially. For example, a variety of functions derived from data on binding of peptides to MHC (Major Histocompatibility Complex) may be used to rescore a library in order to eliminate proteins containing sequences, which can potentially bind to MHC, i.e. potentially immunogenic sequences. See, for example, U.S. Ser. Nos. 60/217,661; 09/903,378; 10/039,170; 60/360,843; 60/384,197; PCT 01/21,823; and PCT 02/00165.

In addition, it should be noted that the preferred methods of the invention result in a rank-ordered or a filtered list of sequences; that is, the sequences are ranked on the basis of some objective criteria. However, as outlined herein, it is possible to create a set of non-ordered sequences, for example by generating a probability table directly (for example using SCMF analysis or sequence alignment techniques) that lists sequences without ranking them. The sampling techniques outlined herein can be used in either situation.

In a preferred embodiment, Boltzmann sampling is done. As will be appreciated by those in the art, the temperature criteria for Boltzmann sampling can be altered to allow broad searches at high temperature and narrow searches close to local optima at low temperatures (see e.g., Metropolis et al., J. Chem. Phys. 21:1087, 1953).

In a preferred embodiment, the sampling technique utilizes genetic algorithms, e.g., such as those described by Holland (Adaptation in Natural and Artificial Systems, 1975, Ann Arbor, U. Michigan Press). Genetic algorithm analysis generally takes generated sequences and recombines them computationally, similar to a nucleic acid recombination event, in a manner similar to "gene shuffling". Thus the "jumps" of genetic algorithm analysis generally are multiple position jumps. In addition, as outlined below, correlated multiple jumps may also be done. Such jumps may occur with different crossover positions and more than one recombination at a time, and may involve recombination of two or more sequences. Furthermore, deletions or insertions (random or biased) can be done. In addition, as outlined below, genetic algorithm analysis may also be used after the secondary library has been generated.

In a preferred embodiment, the sampling technique utilizes simulated annealing, e.g., such as described by Kirkpatrick et al. [Science, 220:671–680 (1983)]. Simulated annealing alters the cutoff for accepting good or bad jumps by altering the temperature. That is, the stringency of the cutoff is altered by altering the temperature. This allows broad searches at high temperature to new areas of sequence space, altering with narrow searches at low temperature to explore regions in detail.

In addition, as outlined below, these sampling methods may be used to further process a first set to generate additional sets of variant TNF-receptor proteins.

As used herein variant TNF-receptor proteins include TNF-R1 (also referred to herein as p55, p55 TNF-R1, p55 TNFR) monomers and TNF-R2 (also referred to herein as p75, p75 TNF-R2) monomers. In addition, these monomers may be dimerized and/or fused to the constant region of an immunoglobulin (or Fc region). Such fusion conjugates may be a fragment or an entire region. See, for example, U.S. Pat. Nos. 5,155,027; 5,567,584; 5,750,375; 5,610,279; 5,843,725; 5,750,375; 5,712,155; 6,018,026; 6,121,022; 6,194,551; 6,277,375; 6,365,161; 6,291,212; 6,291,646; 6,300,099; 6,323,323; U.S. Patent Publication No. 2001/0036459; WO 97/41895; WO 00/42072; and Shields et al. (2001) J. Biol. Chem., 276: 6591–6604; all incorporated by reference.

In a preferred embodiment, the variant TNF-receptor proteins are soluble proteins, preferably monomers, that retain the ability to bind TNF. In a preferred embodiment, the variant TNFR proteins are soluble TNF-R1 monomer variants.

The computational processing results in a set of optimized variant TNF-receptor protein sequences. Optimized variant TNF-receptor protein sequences are generally different from the wild type TNF-receptor sequence in structural regions critical for receptor affinity, i.e, p55 or p75 receptor domains. In a preferred embodiment, "receptor domain(s)" refers to the first three cysteine-rich domains of the extra-cellular region of soluble p55 TNF-R1. Preferably, these three domains are C-terminally fused to an epitope tag (triple flag peptide) for purification purposes. The fourth cysteine-rich domain is generally avoided due to its lack of involvement in TNF binding. A 14 amino acid deletion at the N terminus, which corresponds to residues 1–14 of the crystallized structure, was made between the signal peptide and the first cysteine rich domain (LVPHLGDREKRDSV). The TNFR nomenclature used here is consistent with the description of the crystallized form of the receptor.

Preferably, each optimized variant TNF-receptor protein sequence comprises at least about 1 variant amino acid from the starting or wild-type sequence, with 2–15 being preferred. Preferably, variant TNF-receptor protein sequences comprising 2–5 variant amino acids are generated. However, other embodiments may include TNF-receptor protein sequences comprising from 2–7, 3–5, 5–7, 5–10, 10–15, etc, variant amino acids.

Thus, in the broadest sense, the present invention is directed to variant TNF-receptor proteins that neutralize wild type TNF or antagonize the biological properties of TNF by neutralizing its ability to bind receptors. By "variant TNF-receptor" herein is meant TNF-receptor proteins, which have been designed using the computational methods outlined herein to differ from the corresponding wild type protein by at least 1 amino acid.

By "neutralize", "neutralizing" or other grammatical variations means when a molecule blocks or prevents one molecule from interacting with its target molecule thereby preventing what would otherwise result in some biological response or signal (when present in sufficient amounts). Thus the effect of neutralization is to interfere with the biological response or signal that would normally occur when two molecules interact. A common example would be the ability of a "neutralizing" antibody to block some biological activity of the antigen to which it was raised. Another example occurs when the extra-cellular portion of a cell surface receptor is made soluble and it retains its ability to bind to its ligand. If present in sufficient amounts, this soluble receptor can "neutralize" or block the activity of the ligand.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acd. Sci. U.S.A. 89(20:9367–71 (1992)], generally depending on the method of synthesis. Thus "amino acid", or "peptide residue", as used herein means both naturally occurring and synthetic amino acids. For example, homo-phenylalanine, citrulline, and noreleucine are considered amino acids for the purposes of the invention. "Amino acid" also includes imino acid residues such as proline and hydroxyproline. In addition, any amino acid representing a component of the variant TNF-receptor proteins can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R— or the S—, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes. In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1–2) 68–70 May 22, 1998 and Tang et al., Abstr. Pap Am. Chem. S218:U138-U138 Part 2 Aug. 22, 1999, both of which are expressly incorporated by reference herein.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1–C20.

Acidic amino acids may be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO.sub.3H) threonine, serine, tyrosine.

Other substitutions may include unnatural hydroxylated amino acids which may made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. Preferred alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the variant TNF-receptor polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant TNF-receptor polypeptides of to the present invention may include the following: Cysteinyl residues may be reacted with receptor-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, receptor-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing receptor-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N═C═N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

The TNF-receptor proteins may be from any number of organisms, with TNF-receptor proteins from mammals being particularly preferred. Suitable mammals include, but are not limited to, rodents (rats, mice, hamsters, guinea pigs, etc.), primates, farm animals (including sheep, goats, pigs, cows, horses, etc); and in the most preferred embodiment, from humans. As will be appreciated by those in the art, TNF-receptor proteins based on TNF-receptor proteins from mammals other than humans may find use in animal models of human disease.

The TNF-R proteins of the invention are antagonists of wild type TNF. By "antagonists of wild type TNF" herein is meant that the variant TNF-receptor protein inhibits or significantly decreases the activation of receptor signaling by wild type TNF proteins by at least 10% or more. In a preferred embodiment, the variant TNF-receptor protein interacts with the wild type TNF protein such that the complex comprising the variant TNF-receptor and wild type TNF is incapable of activating TNF receptors, i.e. TNF-R1 or TNF-R2. Preferably, the variant TNF-receptor protein preferentially interacts with wild type TNF such that receptor binding does not occur and/or TNF-receptor signaling is not initiated.

The variant TNF-receptor antagonist proteins of the invention include improved stability, pharmacokinetics, reduced immunogenicity and high affinity for wild type TNF-alpha. Variants with higher affinity, i.e, at least 10% or more, toward wild type TNF-alpha may be generated from variants exhibiting TNF-receptor antagonism as outlined above.

As outlined above, the invention provides variant TNF-receptor nucleic acids encoding variant TNF-receptor polypeptides. The variant TNF-receptor polypeptide preferably has at least one property, i.e., altered property, which is substantially different from the same property of the corresponding naturally occurring TNF polypeptide. The property of the variant TNF-receptor polypeptide is the result the PDA analysis of the present invention.

The term "altered property" or grammatical equivalents thereof in the context of a polypeptide, as used herein, refers to any characteristic or attribute of a polypeptide that can be selected or detected and compared to the corresponding property of a naturally occurring protein. These properties include, but are not limited to cytotoxic activity; oxidative stability, substrate specificity, substrate binding or catalytic activity, thermal stability, alkaline stability, pH activity profile, resistance to proteolytic degradation, kinetic association ($K_{on}$) and dissociation ($K_{off}$) rate, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, a reduction in immunogenicity and the ability to treat disease.

Unless otherwise specified, a substantial change in any of the above-listed properties, when comparing the property of a variant TNF-receptor polypeptide to the property of a naturally occurring TNF-receptor protein is preferably at least a 20%, more preferably, 50%, more preferably at least a 2-fold increase or decrease. Thus, a change in cytotoxic activity is evidenced by at least a 75% or greater decrease in TNF-induced cell death as compared to wild type protein. A change in binding affinity is evidenced by at least a 5% or greater increase or decrease in binding affinity to wild type TNF.

A change in oxidative stability is evidenced by at least about 20%, more preferably at least 50% increase of activity of a variant TNF-receptor protein when exposed to various oxidizing conditions as compared to that of wild type TNF-receptor. Oxidative stability is measured by known procedures.

A change in alkaline stability is evidenced by at least about a 5% or greater increase or decrease (preferably increase) in the half-life of the activity of a variant TNF-receptor protein when exposed to increasing or decreasing pH conditions as compared to that of wild type TNF-receptor. Generally, alkaline stability is measured by known procedures.

A change in thermal stability is evidenced by at least about a 5% or greater increase or decrease (preferably increase) in the half-life of the activity of a variant TNF-receptor protein when exposed to a relatively high temperature and neutral pH as compared to that of wild type TNF-receptor. Generally, thermal stability is measured by known procedures.

Variant TNF-receptor proteins with altered properties are experimentally tested and validated in in vivo and in in vitro assays. Suitable assays include, but are not limited to, inhibition assays, activity assays and binding assays. In a preferred embodiment, binding affinities of variant TNF-receptor proteins as compared to wild type TNF-receptor proteins, such as p55 and p75 are determined. Suitable assays include, but are not limited to, e.g., quantitative comparisons comparing kinetic and equilibrium binding constants. The kinetic association rate ($K_{on}$) and dissociation rate ($K_{off}$), and the equilibrium binding constants ($K_d$) may be determined using surface plasmon resonance on a BIAcore instrument following the standard procedure in the literature [Pearce et al., Biochemistry 38:81–89 (1999)].

In a preferred embodiment, the antigenic profile in the host animal of the variant TNF-receptor protein is similar, and preferably identical, to the antigenic profile of the host TNF-receptor; that is, the variant TNF-receptor protein does not significantly stimulate the host organism (e.g. the patient) to elicit an immune response that is clinically relevant, including allergic responses or neutralization of the protein by an antibody. Thus, in a preferred embodiment, the variant TNF-receptor protein does not contain additional or different epitopes from the wild type TNF-receptor. By "epitope" or "determinant" herein is meant a portion of a protein which will generate and/or bind an antibody. Thus, in most instances, no significant amounts of antibodies are generated to a variant TNF-receptor protein. In general, this is accomplished by not significantly altering surface residues, or by adding any amino acid residues on the surface which can become glycosylated, as novel glycosylation can result in an immune response (as outlined below).

The variant TNF-receptor proteins and nucleic acids of the invention are distinguishable from naturally occurring wild type TNF-receptor. By "naturally occurring" or "wild-type" or grammatical equivalents, herein is meant an amino acid sequence or a nucleotide sequence that is found in nature and includes allelic variations; that is, an amino acid sequence or a nucleotide sequence that usually has not been intentionally modified. Accordingly, by "non-naturally occurring" or "synthetic" or "recombinant" or grammatical equivalents thereof, herein is meant an amino acid sequence or a nucleotide sequence that usually has been intentionally modified using the methods described herein. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the invention. As will be appreciated by those in the art, an alignment of TNF-receptor proteins and variant TNF-receptor proteins may be done using standard programs, as is outlined below, with the identification of "equivalent" positions between the two proteins.

Thus, in a preferred embodiment, the variant TNF-receptor protein has an amino acid sequence that differs from a wild type TNF-receptor sequence by at least 1–5% of the residues. That is, the variant TNF-receptor proteins of the invention are less than about 97–99% identical to a wild type TNF-receptor amino acid sequence. Accordingly, a protein is a "variant TNF-receptor protein" if the overall homology of the protein sequence to the wild type amino acid sequence is preferably less than about 99%, more preferably less than about 98%, even more preferably less than about 97% and more preferably less than 95%. In some embodiments, the homology will be as low as about 75–80%. Stated differently, variant TNF-receptor proteins have at least about 1 residue that differs from the wild type TNF-receptor sequence, with at least about 2, 3, 4, 5, 6, 7, 8, 9, 10, 11, 12, 13, 14, or 15 different residues. Preferred variant TNF-receptor proteins have 3 to 5 different residues.

Homology in this context means sequence similarity or identity, with identity being preferred. As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403–410, (1990); Altschul et al., Nucleic Acids Res. 25:3389–3402 (1997); and Karlin et al., Proc. Natl. Acad. Sci. U.S.A. 90:5873–5787 (1993). A particularly useful BLAST program is the WU-BLAST-2 program which was obtained from Altschul et al., Methods in Enzymology, 266:460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to −22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the wild type sequence, it is understood that in one embodiment, the percentage of sequence identity will be determined based on the number of identical amino acids in relation to the total number of amino acids. Thus, for example, sequence identity of sequences shorter than wild type, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

Thus, the variant TNF-receptor proteins of the present invention may be shorter or longer than the wild type amino acid sequence. Thus, in a preferred embodiment, included within the definition of variant TNF proteins are portions or fragments of the sequences depicted herein. Fragments of variant TNF-receptor proteins are considered variant TNF-receptor proteins if a) they share at least one antigenic epitope; b) have at least the indicated homology; c) and preferably have variant TNF-receptor biological activity as defined herein.

In a preferred embodiment, as is more fully outlined below, the variant TNF-receptor proteins include further amino acid variations, as compared to a wild-type TNF-receptor, than those outlined herein. In addition, as outlined herein, any of the variations depicted herein may be combined in any way to form additional novel variant TNF-receptor proteins.

In addition, variant TNF-receptor proteins may be made that are longer than the wild type sequence, for example, by the addition of epitope or purification tags, as outlined herein, the addition of other fusion sequences, etc. For example, the variant TNF-receptor proteins of the invention may be fused to other therapeutic proteins or to other proteins such as Fc or serum albumin for pharmacokinetic purposes. See for example U.S. Pat. Nos. 5,766,883 and 5,876,969, both of which are expressly incorporated by reference.

In a preferred embodiment, the variant TNF-receptor proteins comprise residues selected from the following positions 65, 66, 67, 69, 72, 75, 77, 78, 79, 80, 105, 107, 108, 111 and 113.

In another preferred embodiment, the variant TNF-receptor proteins comprise non-conservative variants. As used herein, "non-conservative" means substitutions or modifications in the amino acid sequence of a protein which may result in a modified size, charge, polarity and/or activity of the resulting protein. For example, a non-conservative change would include a substitution of a polar amino acid to a non-polar amino acid, rather than a polar to polar change which would be conservative. An example of a non-conservative substitution is histidine to phenylalanine.

In an additional aspect, the non-naturally occurring variant TNF-receptor proteins have substitutions selected from the group of substitutions consisting of N65E, N65F, N65V, H66F, H66K, H66R, H66W, L67F, L67K, H69A, H69D, H69E, H69F, H69K, H69R, H69T, H69Y, H69Q, S72A, S72L, S72G, S72N, S72R, S72Q, K75Q, K75R, R77D, R77K, R77L, R77Q, R77V, K78D, K78R, E79A, E79H, E79K, E79S, E79T, E79W, M80A, M80D, M80E, M80L, H105K, W107A, W107B, W107D, W107E, and W107F. As will be recognized by those skilled in the art, many of the above-described substitutions are non-conservative.

These may be done individually or in combination, with any combination being possible. However, as outlined herein, preferred embodiments utilize at least 1 to 5, and preferably more, positions in each variant TNF-receptor protein.

More specifically, theses variants may be in the form of single point variants, for example, N65F, H66F, H69A, H69D, H69F, H69Y, H69Q, K75R, K78D, M80E, H105K, L67F, S72Q.

In addition, double point variants may be generated including, H66F and H69A, H66F and H69Y, H66F and H69D, $H_{66}F$ and H69Q, H66F and K75R, K75R and H69A, K75R and H69D, K75R and H69Q, K75R and H69Y.

The most preferred double variant is H66F and H69A. Both of these preferred substitutions are non-conservative.

In a preferred embodiment, the variant TNF-receptor proteins of the invention are human TNF-receptor conformers. By "conformer" herein is meant a protein that has a protein backbone 3-D structure that is virtually the same but has significant differences in the amino acid side chains. That is, the variant TNF-receptor proteins of the invention define a conformer set, wherein all of the proteins of the set share a backbone structure and yet have sequences that differ by at least 1–3–5%. The three dimensional backbone structure of a variant TNF-receptor protein thus substantially corresponds to the three-dimensional backbone structure of human TNF-receptor. "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Angstroms RMSD from the human TNF-receptor structure, with no more than 1.5 Angstroms RMSD being preferred, and no more than 1 Angstrom RMSD being particularly preferred. In general, these distances may be determined in two ways. In one embodiment, each potential conformer is crystallized and its three-dimensional structure determined. Alternatively, as the former is quite tedious, the sequence of each potential conformer is run in the PDA™ technology program to determine whether it is a conformer.

Variant TNF-receptor proteins may also be identified as being encoded by variant TNF-receptor nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, a variant TNF-receptor nucleic acid encodes a variant TNF-receptor protein. As will be appreciated by those in the art, due to the degeneracy of the genetic code, an extremely large number of nucleic acids may be made, all of which encode the variant TNF-receptor proteins of the present invention. Thus, having identified a particular amino acid sequence, those skilled in the art could make any number of different nucleic acids, by simply modifying the sequence of one or more codons in a way which does not change the amino acid sequence of the variant TNF-receptor.

In one embodiment, the nucleic acid homology is determined through hybridization studies. Thus, for example, nucleic acids which hybridize under high stringency to a wild type nucleic acid sequence or its complement and encode a variant TNF-receptor protein is considered a variant TNF-receptor gene.

High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10 degrees C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 degrees C. for short probes (e.g. 10 to 50 nucleotides) and at least about 60 degrees C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

The variant TNF-receptor proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated variant TNF-receptor nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild-type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant TNF-receptor protein from one organism in a different organism or host cell. Alternatively, the protein may be made at a significantly higher concentration than is normally seen, through the use of a inducible promoter or high expression promoter, such that the protein is made at increased concentration levels. Furthermore, all of the variant TNF-receptor proteins outlined herein are in a form not normally found in nature, as they contain amino acid substitutions, insertions and deletions, with substitutions being preferred, as discussed below.

Also included within the definition of variant TNF-receptor proteins of the present invention are amino acid sequence variants of the variant TNF-receptor sequences outlined herein. That is, the variant TNF-receptor proteins may contain additional variable positions as compared to human TNF-receptor. These variants fall into one or more of three classes: substitutional, insertional or deletional variants. These variants ordinarily are prepared by site-specific mutagenesis of nucleotides in the DNA encoding a variant TNF-receptor protein, using cassette or PCR mutagenesis or other techniques well known in the art, to produce DNA encoding the variant, and thereafter expressing the DNA in recombinant cell culture as outlined above. However, variant TNF-receptor protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the variant TNF-receptor protein amino acid sequence. The variants typically exhibit the same qualitative biological activity as the naturally occurring analogue; although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variant TNF-receptor proteins screened for the optimal combination of desired activity. Techniques for making substitution mutations at predetermined sites in DNA having a known sequence are well known, for example, M13 primer mutagenesis and PCR mutagenesis. Screening of the mutants is done using assays of variant TNF-receptor protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Substantial changes in function or immunological identity are made by selecting substitutions that are less conservative or non-conservative. For example, substitutions may be made which more significantly affect: the structure of the polypeptide backbone in the area of the alteration, for example the receptor-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. Thus, the methods of the present invention can be used to modulate the immunogenicity of the variant TNF-receptor proteins. Preferably, the immunogenicity of the variant TNF-receptor proteins is reduced. By "reduced" herein is meant that at least one immunological response is decreased relative to the wild-type protein.

The variants typically exhibit the same qualitative biological activity and will elicit the same immune response as the original variant TNF-receptor protein, although variants also are selected to modify the characteristics of the variant TNF-receptor proteins as needed. Alternatively, the variant may be designed such that the biological activity of the variant TNF-receptor protein is altered. For example, glycosylation sites may be altered or removed. Similarly, the biological function may be altered; for example, in some instances it may be desirable to have more or less potent TNF-receptor activity.

Soluble p55 variant TNF proteins and nucleic acids are the most preferred embodiments. In this embodiment, the soluble p55 variant TNF can serve as an antagonist to receptor signaling. By "serving as an antagonist to receptor signaling" herein is meant that the soluble p55 variant TNF proteins preferentially interact with wild type TNF to block or significantly decrease TNF-receptor activated signaling.

Thus, the computational processing results described above may be used to generate a set of optimized variant p55 protein sequences. Optimized variant p55 protein sequences are generally different from wild type p55 sequences in at least about 1 variant amino acid.

In a preferred embodiment variant TNF p55 proteins are fused to a human TNF receptor-associated factor (TRAF) trimerization domain. In a preferred embodiment, the C termini of optimized variant TNF p 55 receptors will be fused to TRAF trimerization domains (i.e., leucine zipper motif). Fusion of trimerization domains from TRAF proteins to TNFR molecules can induce trimerization, resulting in higher avidity for TNF-receptor thereby creating a more potent TNF-receptor inhibitor than the monomeric soluble TNFR. These trimerization domains can be used to induce the trimerization of any protein where this may be desirable, including TNF beta, TNF receptor (p55 and p75), and other members of the TNF receptor family including NGF receptor, CD27, CD30, CD40, fas antigen. Other peptides that are known to form trimeric coiled coils could also be used, including pil (Harbury, Kim and Alber, 1994).

The variant TNF-receptor proteins and nucleic acids of the invention can be made in a number of ways. Individual nucleic acids and proteins can be made as known in the art and outlined below. Alternatively, libraries of variant TNF-receptor proteins can be made for testing.

As will be appreciated, a variant TNF-receptor library created by recombining variable positions and/or residues at the variable position may not be in a filtered list. In some embodiments, the entire list may just be made and tested. Alternatively, in a preferred embodiment, the variant TNF-receptor library is also in the form of a filtered list. This may be done for several reasons, including the size of the library is still too big to generate experimentally, or for predictive purposes. This may be done in several ways. In one embodiment, the library is generated using the scoring functions of the PDA™ technology to list the library members. Alternatively, statistical methods may be used. For example, the library may be ranked by frequency score; that is, proteins containing the most of high frequency residues could be ranked higher, etc. This may be done by adding or multiplying the frequency at each variable position to generate a numerical score. Similarly, the library different positions may be weighted and then the proteins scored; for example, those containing certain residues could be arbitrarily ranked.

In a preferred embodiment, the different protein members of the variant TNF-receptor library may be chemically synthesized. This is particularly useful when the designed proteins are short, preferably less than 150 amino acids in length, with less than 100 amino acids being preferred, and less than 50 amino acids being particularly preferred, although as is known in the art, longer proteins may be made chemically or enzymatically. See for example Wilken et al, Curr. Opin. Biotechnol. 9:412–26 (1998), hereby expressly incorporated by reference.

In a preferred embodiment, particularly for longer proteins or proteins for which large samples are desired, the library sequences are used to create nucleic acids such as DNA which encode the member sequences and which may then be cloned into host cells, expressed and assayed, if desired. Thus, nucleic acids, and particularly DNA, may be made which encodes each member protein sequence. This is done using well known procedures. The choice of codons, suitable expression vectors and suitable host cells will vary depending on a number of factors, and may be easily optimized as needed.

In a preferred embodiment, multiple PCR reactions with pooled oligonucleotides are done, as is generally described in U.S. Ser. No. 09/981,289, incorporated herein by reference. In this embodiment, overlapping oligonucleotides are synthesized which correspond to the full-length gene. Again, these oligonucleotides may represent all of the different amino acids at each variant position or subsets.

In a preferred embodiment, these oligonucleotides are pooled in equal proportions and multiple PCR reactions are performed to create full-length sequences containing the combinations of mutations defined by the library. In addition, this may be done using error-prone PCR methods.

In a preferred embodiment, the different oligonucleotides are added in relative amounts corresponding to the probability distribution table. The multiple PCR reactions thus result in full length sequences with the desired combinations of mutations in the desired proportions.

The total number of oligonucleotides needed is a function of the number of positions being mutated and the number of mutations being considered at these positions:

(number of oligos for constant positions)+M1+M2+M3+ Mn=(total number of oligos required), where Mn is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo may contain the codon for a single position being mutated, or for more than one position being mutated. The multiple positions being mutated must be close in sequence to prevent the oligo length from being impractical. For multiple mutating positions on an oligonucleotide, particular combinations of mutations may be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster". When the clusters are comprised of residues close together, and thus can reside on one oligonucleotide primer, the clusters can be set to the "good" correlations, and eliminate the bad combinations that may decrease the effectiveness of the library. However, if the residues of the cluster are far apart in sequence, and thus will reside on different oligonucleotides for synthesis, it may be desirable to either set the residues to the "good" correlation, or eliminate them as variable residues entirely. In an alternative embodiment, the library may be generated in several steps, so that the cluster mutations only appear together. This procedure, i.e. the procedure of identifying mutation clusters and either placing them on the same oligonucleotides or eliminating them from the library or library generation in several steps preserving clusters, can considerably enrich the experimental library with properly folded protein. Identification of clusters may be carried out by a number of ways, e.g. by using known pattern recognition methods, comparisons of frequencies of occurrence of mutations or by using energy analysis of the sequences to be experimentally generated (for example, if the energy of interaction is high, the positions are correlated). These correlations may be positional correlations (e.g. variable positions 1 and 2 always change together or never change together) or sequence correlations (e.g. if there is residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford University, 1999; Andrews, Harry C. Introduction to mathematical techniques in pattern recognition; New York, Wiley-Interscience [1972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with neural networks in C++/Abhijit S. Pandya, Robert B. Macy. Boca Raton, Fla.: CRC Press, 1996; Handbook of pattern recognition & computer vision/edited by C. H. Chen, L. F. Pau, P. S. P. Wang. 2nd ed. Singapore; River Edge, N.J.: World Scientific, c1999; Friedman, Introduction to Pattern Recognition: Statistical, Structural, Neural, and Fuzzy Logic Approaches; River Edge, N.J.: World Scientific, c1999, Series title: Series in machine perception and artificial intelligence; vol. 32; all of which are expressly incorporated by reference. In addition, programs used to search for consensus motifs can be used as well.

In addition, correlations and shuffling can be fixed or optimized by altering the design of the oligonucleotides; that is, by deciding where the oligonucleotides (primers) start and stop (e.g. where the sequences are "cut"). The start and stop sites of oligos can be set to maximize the number of clusters that appear in single oligonucleotides, thereby enriching the library with higher scoring sequences. Different oligonucleotide start and stop site options can be computationally modeled and ranked according to number of clusters that are represented on single oligos, or the percentage of the resulting sequences consistent with the predicted library of sequences.

The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons may be used to create a library expressing different length proteins. In particular computational sequence screening for insertions or deletions may result in secondary libraries defining different length proteins, which can be expressed by a library of pooled oligonucleotide of different lengths.

In a preferred embodiment, the variant TNF-receptor library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are expressly incorporated by reference in their entirety. This set of sequences may also be an artificial set; for example, from a probability table (for example generated using SCMF) or a Monte Carlo set. Similarly, the "family" can be the top 10 and the bottom 10 sequences, the top 100 sequence, etc. This may also be done using error-prone PCR.

Thus, in a preferred embodiment, in silico shuffling is done using the computational methods described herein. That is, starting with either two libraries or two sequences, random recombinations of the sequences may be generated and evaluated.

In a preferred embodiment, error-prone PCR is done to generate the variant TNF-receptor library. See U.S. Pat. Nos. 5,605,793, 5,811,238, and 5,830,721, all of which are hereby incorporated by reference. This may be done on the optimal sequence or on top members of the library, or some other artificial set or family. In this embodiment, the gene for the optimal sequence found in the computational screen of the primary library may be synthesized. Error-prone PCR is then performed on the optimal sequence gene in the presence of oligonucleotides that code for the mutations at the variant positions of the library (bias oligonucleotides). The addition of the oligonucleotides will create a bias favoring the incorporation of the mutations in the library. Alternatively, only oligonucleotides for certain mutations may be used to bias the library.

In a preferred embodiment, gene shuffling with error-prone PCR can be performed on the gene for the optimal sequence, in the presence of bias oligonucleotides, to create a DNA sequence library that reflects the proportion of the mutations found in the variant TNF-receptor library. The choice of the bias oligonucleotides can be done in a variety of ways; they can chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions may be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild-type gene or other gene may be used (see also U.S. Ser. No. 09/981,289; incorporated herein by reference in its entirety). In this embodiment, a starting gene is used; generally, although this is not required, the gene is usually the wild-type gene. In some cases it may be the gene encoding the global optimized sequence, or any other sequence of the list, or a consensus sequence obtained e.g. from aligning homologous sequences from different organisms. In this embodiment, oligonucleotides are used that correspond to the variant positions and contain the different amino acids of the library. PCR is done using PCR primers at the termini, as is known in the art. This provides two benefits. First, this generally requires fewer oligonucleotides and may result in fewer errors. Second, it has experimental advantages in that if the wild-type gene is used, it need not be synthesized.

In addition, there are several other techniques that may be used, as described in U.S. Ser. No. 09/981,289. In a preferred embodiment, ligation of PCR products is done.

In a preferred embodiment, a variety of additional steps may be done to the variant TNF-receptor library; for example, further computational processing may occur, different variant TNF-receptor libraries can be recombined, or cutoffs from different libraries may be combined. In a preferred embodiment, a variant TNF-receptor library may be computationally remanipulated to form an additional variant TNF-receptor library (sometimes referred to herein as "tertiary libraries"). For example, any of the variant TNF-receptor library sequences may be chosen for a second round of PDA, by freezing or fixing some or all of the changed positions in the first library. Alternatively, only changes seen in the last probability distribution table are allowed. Alternatively, the stringency of the probability table may be altered, either by increasing or decreasing the cutoff for inclusion. Similarly, the variant TNF-receptor library may be recombined experimentally after the first round; for example, the best gene/genes from the first screen may be taken and gene assembly redone (using techniques outlined below, multiple PCR, error-prone PCR, shuffling, etc.). Alternatively, the fragments from one or more good gene(s) to change probabilities at some positions. This biases the search to an area of sequence space found in the first round of computational and experimental screening. See, U.S. Pat. No. 6,403,312; U.S. Ser. No. 09/782,004; 09/927,790; and 10/218,102, all hereby incorporated by reference.

In a preferred embodiment, a tertiary library may be generated from combining different variant TNF-receptor libraries. For example, a probability distribution table from a first variant TNF-receptor library may be generated and recombined, either computationally or experimentally, as outlined herein. A PDA variant TNF-receptor library may be combined with a sequence alignment variant TNF-receptor library, and either recombined (again, computationally or experimentally) or just the cutoffs from each joined to make a new tertiary library. The top sequences from several libraries may be recombined. Sequences from the top of a library may be combined with sequences from the bottom of the library to more broadly sample sequence space, or only sequences distant from the top of the library may be combined. Variant TNF-receptor libraries that analyzed different parts of a protein may be combined to a tertiary library that treats the combined parts of the protein.

In a preferred embodiment, a tertiary library may be generated using correlations in a variant TNF-receptor library. That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation.

Using the nucleic acids of the present invention which encode a variant TNF-receptor protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant TNF-receptor protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In another embodiment, when the endogenous secretory sequence leads to a low level of secretion of the naturally occurring protein or of the variant TNF-receptor protein, a replacement of the naturally occurring secretory leader sequence is desired. In this embodiment, an unrelated secretory leader sequence is operably linked to a variant TNF-receptor encoding nucleic acid leading to increased protein secretion. Thus, any secretory leader sequence resulting in enhanced secretion of the variant TNF-receptor protein, when compared to the secretion of TNF-receptor and its secretory sequence, is desired. Suitable secretory leader sequences that lead to the secretion of a protein are known in the art.

In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

In a preferred embodiment, the expression vector comprises the components described above and a gene encoding a variant TNF-receptor protein. As will be appreciated by those in the art, all combinations are possible and accordingly, as used herein, the combination of components, comprised by one or more vectors, which may be retroviral or not, is referred to herein as a "vector composition".

The variant TNF-receptor nucleic acids are introduced into the cells either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The variant TNF-receptor nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The variant TNF-receptor proteins of the present invention are produced by culturing a host cell transformed with an expression vector containing nucleic acid encoding a variant TNF-receptor protein, under the appropriate conditions to induce or cause expression of the variant TNF-receptor protein. The conditions appropriate for variant TNF-receptor protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, *Neurospora*, BHK, CHO, COS, *Pichia Pastoris*, etc.

In another preferred embodiment, the variant TNF-receptor proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase 11 to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, HEK, 293T cells, NIH3T3 cells, CHO, Cos, etc. See the ATCC cell line catalog, hereby expressly incorporated by reference.

In one embodiment, the cells may be additionally genetically engineered, that is, contain exogenous nucleic acid other than the variant TNF-receptor nucleic acid.

In a preferred embodiment, the variant TNF-receptor proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the variant TNF-receptor protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences or the pET system (see U.S. Pat. No. 4,952,496 and Rodseth, L. E. et al. (1994) J. Mol. Biol. 239:332–335, both hereby incorporated by reference).

For example, a gene of interest is cloned into a vector (e.g., pET) which contains a selectable marker (e.g., ampicillin resistance) and lies downstream of a highly specific promoter (e.g., T7 RNA polymerase). The vector is propagated under drug selection (ampicillin) in an $E$ $coli$ host which does not contain a T7 RNA polymerase gene (i.e., a non-expressing host). Expression of the gene of interest may be achieved by transferring the plasmid into a second $E$ $coli$ host (expression host) which contains a chromosomal copy of the T7 RNA polymerase. This polymerase is kept under the control of a separate inducible repressor/promoter system well known in the art (e.g., lacUV5) allowing for a sequential regulation of protein expression of the gene of interest.

Upon successful introduction of the recombinant plasmid into the bacterial expression host, the bacteria are allowed to grow to an appropriate density (e.g., mid-log growth phase, OD650 nM=0.8).

Expression of the T7 RNA polymerase is induced by adding IPTG to the growth media. Its subsequent expression then drives transcription of the gene of interest in a tightly regulated manner. This induction is carried out for a particular period of time and at a specific temperature which can be deduced for each gene. The bacteria can be harvested by known methods (centrifugation) and lysed. For certain proteins deemed insoluble, expression in $E$ $coli$ can result in their being compartmentalized by the bacteria into inclusion bodies. These inclusion bodies can be isolated from the rest of the bacterial components (e.g., centrifugation) and this constitutes a step in their being isolated to purity.

Furthermore, a bacterial promoter may include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others. As is typical for procaryotic expression of proteins, the protein is expressed in inclusion bodies and requires refolding. Purification and refolding of the protein from the inclusion bodies is well known in the art.

The bacterial expression vectors are transformed into bacterial host cells using techniques well known in the art, such as calcium chloride treatment, electroporation, and others.

In one embodiment, variant TNF-receptor proteins are produced in insect cells. Expression vectors for the transformation of insect cells, and in particular, baculovirus-based expression vectors, are well known in the art.

In a preferred embodiment, variant TNF-receptor protein is produced in yeast cells. Yeast expression systems are well known in the art, and include expression vectors for *Sac-* charomyces cerevisiae, Candida albicans and C. maltosa, Hansenula polymorpha, Kluyveromyces fragilis and K. lactis, Pichia guillerimondii and P. pastoris, Schizosaccharomyces pombe, and Yarrowia lipolytica. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In a preferred embodiment, modified TNF-receptor variants are covalently coupled to at least one additional TNF-receptor variant via a linker to improve the antagonist activity. A number of strategies may be used to covalently link modified receptor domains together. These include, but are not limited to, linkers, such as polypeptide linkages between N- and C-termini of two domains, linkage via a disulfide bond between monomers, and linkage via chemical cross-linking reagents. Alternatively, the N- and C-termini may be covalently joined by deletion of portions of the N- and/or C-termini and linking the remaining fragments via a linker or linking the fragments directly.

By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. In one aspect of this embodiment, the linker is a peptide bond. Choosing a suitable linker for a specific case where two polypeptide chains are to be connected depends on various parameters, e.g., the nature of the two polypeptide chains (e.g., whether they naturally oligomerize (e.g., form a dimer or not), the distance between the N- and the C-termini to be connected if known from three-dimensional structure determination, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. These linked TNF-receptor proteins have constrained hydrodynamic properties, that is, they form constitutive dimers) and thus efficiently interact to reduce or neutralize the signaling pathways or the biological effects thereof.

The linker peptide should have a length that is adequate to link two TNF-receptor variant monomers in such a way that they assume the correct conformation relative to one another so that they retain the desired activity as antagonists of the TNF receptor. Suitable lengths for this purpose include at least one and not more than 30 amino acid residues. Preferably, the linker is from about 1 to 30 amino acids in length, with linkers of 1, 2, 3, 4, 5, 6, 7, 8, 9, 10, 11, 12, 13, 14, 15, 16, 17, 18 19 and 20 amino acids in length being preferred. See also WO 01/25277, incorporated herein by reference in its entirety.

In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains.

Useful linkers include glycine-serine polymers (including, for example, $(GS)_n$, $(GSGGS)_n$ $(GGGGS)_n$ and $(GGGS)_n$, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

Suitable linkers may also be identified by screening databases of known three-dimensional structures for naturally occurring motifs that can bridge the gap between two polypeptide chains. Another way of obtaining a suitable linker is by optimizing a simple linker, e.g., $(Gly_4Ser)_n$, through random mutagenesis. Alternatively, once a suitable polypeptide linker is defined, additional linker polypeptides can be created by application of PDA™ technology to select amino acids that more optimally interact with the domains being linked. Other types of linkers that may be used in the present invention include artificial polypeptide linkers and inteins. In another preferred embodiment, disulfide bonds are designed to link the two receptor monomers at inter-monomer contact sites. In one aspect of this embodiment the two receptors are linked at distances <5A. In addition, the variant TNF-receptor polypeptides of the invention may be further fused to other proteins, if desired, for example to increase expression or stabilize the protein.

In one embodiment, the variant TNF-receptor nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the variant TNF-receptor proteins may be covalently modified. Covalent and non-covalent modifications of the protein are thus included within the scope of the present invention. Such modifications may be introduced into a variant TNF-receptor polypeptide by reacting targeted amino acid residues of the polypeptide with an organic derivatizing agent that is capable of reacting with selected side chains or terminal residues.

One type of covalent modification includes reacting targeted amino acid residues of a variant TNF-receptor polypeptide with an organic derivatizing agent that is capable of reacting with selected side chains or the N- or C-terminal residues of a variant TNF-receptor polypeptide. Derivatization with bifunctional agents is useful, for instance, for cross linking a variant TNF-receptor protein to a water-insoluble support matrix or surface for use in the method for purifying anti-variant TNF-receptor antibodies or screening assays, as is more fully described below. Commonly used cross linking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W.H. Freeman & Co., San Francisco, pp. 79–86 (1983)], acetylation of the N-terminal amine, and amidation of any C-terminal carboxyl group.

Another type of covalent modification of the variant TNF-receptor polypeptide included within the scope of this invention comprises altering the native glycosylation pattern of the polypeptide. "Altering the native glycosylation pattern" is intended for purposes herein to mean deleting one or more carbohydrate moieties found in native sequence variant TNF-receptor polypeptide, and/or adding one or more glycosylation sites that are not present in the native sequence variant TNF-receptor polypeptide.

Addition of glycosylation sites to variant TNF-receptor polypeptides may be accomplished by altering the amino acid sequence thereof. The alteration may be made, for example, by the addition of, or substitution by, one or more serine or threonine residues to the native sequence variant TNF-receptor polypeptide (for O-linked glycosylation sites). The variant TNF-receptor amino acid sequence may optionally be altered through changes at the DNA level, particularly by mutating the DNA encoding the variant TNF-receptor polypeptide at preselected bases such that codons are generated that will translate into the desired amino acids.

Another means of increasing the number of carbohydrate moieties on the variant TNF-receptor polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259–306 (1981).

Removal of carbohydrate moieties present on the variant TNF-receptor polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Such derivatized moieties may improve the solubility, absorption, and permeability across the blood brain barrier biological half life, and the like. Such moieties or modifications of variant TNF-receptor polypeptides may alternatively eliminate or attenuate any possible undesirable side effect of the protein and the like. Moieties capable of mediating such effects are disclosed, for example, in Remington's Pharmaceutical Sciences, 16th ed., Mack Publishing Co., Easton, Pa. (1980).

Another type of covalent modification of variant TNF-receptor comprises linking the variant TNF-receptor polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

In another preferred embodiment, cysteines are designed into variant or wild-type TNF-receptor in order to incorporate (a) labeling sites for characterization and (b) incorporate PEGylation sites. For example, labels that may be used are well know n in the art and include but are not limited to biotin, tag and fluorescent labels (e.g. fluorescein). These labels may be used in various assays as are also well known in the art to achieve characterization.

Optimal sites for modification can be chosen using a variety of criteria, including but not limited to, visual inspection, structural analysis, sequence analysis and molecular simulation. For example, the fractional accessibility of individual residues was analyzed to identify mutational sites that will not disrupt the monomer structure. Then the minimum distance from each side chain of a monomer to another subunit was calculated to ensure that chemical modification will not disrupt activity. It is possible that receptor binding disruption may occur and may be beneficial to the activity of the TNFR1 variants of this invention.

More specifically, removal or deletion of from about 1 to about 55 amino acids from either the N or C termini, or both are preferred. A more preferred embodiment includes deletions of N-termini beyond residue 10 and more preferably, deletion of the first 47 N-terminal amino acids. The deletion of C-terminal leucine is an alternative embodiment.

Variant TNF-receptor polypeptides of the present invention may also be modified in a way to form chimeric molecules comprising a variant TNF-receptor polypeptide fused to another, heterologous polypeptide or amino acid sequence. In one embodiment, such a chimeric molecule comprises a fusion of a variant TNF-receptor polypeptide (preferably in dimerized form) with a tag polypeptide which provides an epitope to which an anti-tag antibody can selectively bind. The epitope tag is generally placed at the amino-or carboxyl-terminus of the variant TNF-receptor polypeptide. The presence of such epitope-tagged forms of a variant TNF-receptor polypeptide can be detected using an antibody against the tag polypeptide. Also, provision of the epitope tag enables the variant TNF-receptor polypeptide to be readily purified by affinity purification using an anti-tag antibody or another type of affinity matrix that binds to the epitope tag. In an alternative embodiment, the chimeric molecule may comprise a fusion of a variant TNF-receptor polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol. 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology 6:1204–1210 (1988)]; the KT3 epitope peptide [Martin et al., Science 255:192–194 (1992)]; tubulin epitope peptide [Skinner et al., J. Biol. Chem. 266:15163–15166 (1991)]; and the T7 gene 10 protein peptide tag [Lutz-Freyermuth et al., Proc. Natl. Acad. Sci. U.S.A. 87:6393–6397 (1990)].

In a preferred embodiment, the variant TNF-receptor protein is purified or isolated after expression. Variant TNF-receptor proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the variant TNF-receptor protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the variant TNF-receptor protein. In some instances no purification will be necessary.

Once made, the variant TNF-receptor proteins and nucleic acids of the invention find use in a number of applications. In a preferred embodiment, the variant TNF-receptor proteins are administered to a patient to treat an TNF-receptor related disorder.

By "TNF related disorder" or "TNF responsive disorder" or "condition" herein is meant a disorder that may be ameliorated by the administration of a pharmaceutical composition comprising a variant TNF-receptor protein, including, but not limited to, inflammatory and immunological disorders. In a preferred embodiment, the variant TNF-receptor protein is used to treat rheumatoid arthritis, inflammatory bowel diseases, sepsis and septic shock, peripheral nerve injury or demyelinating diseases.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The term "treatment" in the instant invention is meant to include therapeutic treatment, as well as prophylactic, or suppressive measures for the disease or disorder. Thus, for example, successful administration of a variant TNF-receptor protein prior to onset of the disease results in "treatment" of the disease. As another example, successful administration of a variant TNF-receptor protein after clinical manifestation of the disease to combat the symptoms of the disease comprises "treatment" of the disease. "Treatment" also encompasses administration of a variant TNF-receptor protein after the appearance of the disease in order to eradicate the disease. Successful administration of an agent after onset and after clinical symptoms have developed, with possible abatement of clinical symptoms and perhaps amelioration of the disease, comprises "treatment" of the disease.

Those "in need of treatment" include mammals already having the disease or disorder, as well as those prone to having the disease or disorder, including those in which the disease or disorder is to be prevented.

In another embodiment, a therapeutically effective dose of a variant TNF-receptor protein, a variant TNF-receptor gene, or a variant TNF-receptor antibody is administered to a patient having a disease involving inappropriate expression of TNF-receptor. A "disease involving inappropriate expression of TNF" within the scope of the present invention is meant to include diseases or disorders characterized by aberrant TNF, either by alterations in the amount of TNF present or due to the presence of variant TNF-receptor. An overabundance may be due to any cause, including, but not limited to, overexpression at the molecular level, prolonged or accumulated appearance at the site of action, or increased activity of TNF-receptor relative to normal. Included within this definition are diseases or disorders characterized by a reduction of TNF. This reduction may be due to any cause, including, but not limited to, reduced expression at the molecular level, shortened or reduced appearance at the site of action, mutant forms of TNF-receptor, or modulation of activity of TNF-receptor relative to normal. Such an overabundance or reduction of TNF can be measured relative to normal expression, appearance, or activity of TNF or its TNF-receptor according to, but not limited to, the assays described and referenced herein.

The administration of the variant TNF-receptor proteins of the present invention, preferably in the form of a sterile aqueous solution, may be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds, inflammation, etc., the variant TNF-receptor protein may be directly applied as a solution or spray. Depending upon the manner of introduction, the pharmaceutical composition may be formulated in a variety of ways. The concentration of the therapeutically active variant TNF-receptor protein in the formulation may vary from about 0.1 to 100 weight %. In another preferred embodiment, the concentration of the variant TNF-receptor protein is in the range of 0.003 to 1.0 molar, with dosages from 0.03, 0.05, 0.1, 0.2, and 0.3 millimoles per kilogram of body weight being preferred.

The pharmaceutical compositions of the present invention comprise a variant TNF-receptor protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations.

In a further embodiment, the variant TNF-receptor proteins are added in a micellular formulation; see U.S. Pat. No. 5,833,948, hereby expressly incorporated by reference in its entirety.

Combinations of pharmaceutical compositions may be administered. Moreover, the compositions may be administered in combination with other therapeutics.

In one embodiment provided herein, antibodies, including but not limited to monoclonal and polyclonal antibodies, are raised against variant TNF-receptor proteins using methods known in the art. In a preferred embodiment, these anti-variant TNF-receptor antibodies are used for immunotherapy. Thus, methods of immunotherapy are provided. By "immunotherapy" is meant treatment of an TNF-receptor related disorders with an antibody raised against a variant TNF-receptor protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a variant TNF-receptor protein antigen to which antibodies are raised. As appreciated by one of ordinary skill in the art, the variant TNF-receptor protein antigen may be provided by injecting a variant TNF-receptor polypeptide against which antibodies are desired to be raised into a recipient, or contacting the recipient with a variant TNF-receptor protein encoding nucleic acid, capable of expressing the variant TNF-receptor protein antigen, under conditions for expression of the variant TNF-receptor protein antigen.

In another preferred embodiment, a therapeutic compound is conjugated to an antibody, preferably an anti-variant TNF-receptor protein antibody. The therapeutic compound may be a cytotoxic agent. In this method, targeting the cytotoxic agent to tumor tissue or cells, results in a reduction in the number of afflicted cells, thereby reducing symptoms associated with cancer, and variant TNF-receptor protein related disorders. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, variant TNF-receptor proteins are administered as therapeutic agents, and can be formulated as outlined above. Similarly, variant TNF-receptor genes (including both the full-length sequence, partial sequences, or regulatory sequences of the variant TNF-receptor coding regions) may be administered in gene therapy applications, as is known in the art. These variant TNF-receptor genes can include antisense applications, either as gene therapy (i.e. for incorporation into the genome) or as antisense compositions, as will be appreciated by those in the art.

In a preferred embodiment, the nucleic acid encoding the variant TNF-receptor proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. [Zamecnik et al., Proc. Natl. Acad. Sci. U.S.A. 83:4143–4146 (1986)]. The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., Trends in Biotechnology 11:205–210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429–4432 (1987); and Wagner et al., Proc. Natl. Acad. Sci. U.S.A. 87:3410–3414 (1990). For review of gene marking and gene therapy protocols see Anderson et al., Science 256:808–813 (1992).

In a preferred embodiment, variant TNF-receptor genes are administered as DNA vaccines, either single genes or combinations of variant TNF-receptor genes. Naked DNA vaccines are generally known in the art. Brower, Nature Biotechnology, 16:1304–1305 (1998). Methods for the use of genes as DNA vaccines are well known to one of ordinary skill in the art, and include placing a variant TNF-receptor gene or portion of a variant TNF-receptor gene under the control of a promoter for expression in a patient in need of treatment. The variant TNF-receptor gene used for DNA vaccines can encode full-length variant TNF-receptor proteins, but more preferably encodes portions of the variant TNF-receptor proteins including peptides derived from the variant TNF-receptor protein. In a preferred embodiment a patient is immunized with a DNA vaccine comprising a plurality of nucleotide sequences derived from a variant TNF-receptor gene. Similarly, it is possible to immunize a patient with a plurality of variant TNF-receptor genes or portions thereof as defined herein. Without being bound by theory, expression of the polypeptide encoded by the DNA vaccine, cytotoxic T-cells, helper T-cells and antibodies are induced which recognize and destroy or eliminate cells expressing TNF-receptor proteins.

In a preferred embodiment, the DNA vaccines include a gene encoding an adjuvant molecule with the DNA vaccine. Such adjuvant molecules include cytokines that increase the immunogenic response to the variant TNF-receptor polypeptide encoded by the DNA vaccine. Additional or alternative adjuvants are known to those of ordinary skill in the art and find use in the invention.

All references cited herein, including patents, patent applications (provisional, utility and PCT), and publications are incorporated by reference in their entirety.

EXAMPLES

Antagonist Activity of Flag TNF-R Library

Prior to determining variant activity, an immuno-assay to quantitate the amount of variant TNFR in the conditioned media from cells expressing variant TNFR was performed.

96 well plates were coated with anti-Flag monoclonal antibody (2.5 ug/ml) 100 ul per well, followed by 3% BSA/PBS BSA blocking. Control and TNFR samples were then added for a prescribed time (2 hr). Wild Type Flag TNF R of known quantity was used as a standard in the ELISA. A 3 point dilution of each variant was made to ensure reliable quantitation. After washing the plates with phospho-buffered saline, goat anti-human TNF R antibody (2 ug/ml) 100 ul per well was added for a prescribed time (1 hr). The plates were washed 6 times with PBS and an anti-goat alkaline phosphatase-conjugated antibody was added 1/10,000 dilution (X ug/ml) 100 ul per well. Following a prescribed incubation (1 hr) the plates were washed with PBS and the ELISA was completed by adding a luminescence substrate 100 ul per well and reading Luminescence or RLU measurements.

Based on concentrations obtained, each TNF R variant was normalized to 50 ng/mL. A four point dilution series was made for each variant. To determine the antagonist activity of TNFR variants, TNF-induced caspase-3 activation was measured. Caspase-3 activation of mouse WEHI-3 cells was achieved by priming the cells with 1 ug/ml actinomycin D and treating with 10 ng/mL of TNF for 4 hrs.

Antagonist activity of variant TNF R1 was determined by measuring the inhibition of TNFa induced caspase activity described above in the presence (or absence) of TNFR variants. Comparison of the antagonist activity of WT TNF R1 to variant TNF R1 expressed in mammalian cells allowed for determining relative potency. The following procedure was used:

0.05 ml of media containing $5\times10^5$ WEHI 13 var *cells* was added to each well of a 96 well plate 24 hours prior to the experiment. The plate was incubated overnight at 37° C. in a humidified chamber with 5% CO2. On the day of the experiment, 2× assay media was prepared by adding actinomycin D (2 ug/mL) and TNFa (20 ng/ml) to cell culture media. Serial dilutions of commercial and variant TNF R1 were pre-mixed in assay media at the appropriate concentrations. The range of the TNFR1 standard tested was 31 μg/ml to 31 pg/mL. Upon pre-mixing of TNFa assay media to the variant TNFR1, an equal volume of sample was added immediately to the WEHI cells. The assay proceeded for 4 hours at 37° C. in a humidified chamber with 5% CO2. Caspase substrate was then added and incubated for an additional 2 hours at 37° C. in a humidified chamber with 5% CO2. Caspase activity was determined by measuring fluorescence at 485 nm/535 nm, 1.0 second/well. The results of this assay are shown in FIG. 2.

Whereas particular embodiments of the invention have been described above for purposes of illustration, it will be appreciated by those skilled in the art that numerous variations of the details may be made without departing from the invention as described in the appended claims.

We claim:

1. An isolated Tumor Necrosis Factor (TNF)-receptor protein comprising an amino acid sequence comprising at least one amino acid substitution as compared to amino acids 15–138 of SEQ ID NO: 1, wherein said amino acid substitution is selected from the group consisting of positions: 65, 66, 67, 69, 72, 75, 77, 78, 79, 80, 105, 107, 108, 111 and 113.

2. An isolated TNF-receptor protein according to claim 1, wherein said TNF-receptor protein has from 2 to 5 amino acid substitutions as compared to said amino acids 15–138 of SEQ ID NO: 1.

3. A TNF-receptor protein according to claim 1, wherein said TNF-receptor protein has enhanced antagonistic properties as compared to SEQ ID NO: 1.

4. A TNF-receptor protein according to claims 1, 2 or 3 wherein said TNF-receptor protein has reduced immunogenicity.

5. A TNF-receptor protein according to claim 1, wherein said substitution is selected from the group consisting of N65E, N65F, N65V, H66F, H66K, H66R, H66W, L67F, L67K, H69A, H69D, H69E, H69F, H69K, H69R, H69T, H69Y, H69Q, S72A, S72L, S72G, S72N, S72R, S72Q, K75Q, K75R, R77D, R77K, R77L, R77Q, R77V, K78D, K78R, E79A, E79H, E79K, E79S, E79T, E79W, M80A, M80D, M80E, M80L, H105K, W107A, W107B, W107D, W107E, W107F and combinations thereof.

6. A TNF-receptor protein according to claim 5, wherein said substitutions are selected from the group consisting of: N65F, H66F, H69A, H69D, H69F, H69Y, H69Q, K75R, K78D, M80E, H105K, L67F, S72Q and combinations thereof.

7. A TNF-receptor protein according to claim 6, wherein said TNF-receptor protein is a double point variant having substitutions selected from the group consisting of H66F and H69A, H66F and H69Y, H66F and H69D, H66F and H69Q, H66F and K75R, K75R and H69A, K75R and H69D, K75R and H69Q, and K75R and H69Y.

8. A TNF-receptor protein according to claim 7, wherein said double point variant comprises H66F and either H69A or H69D.

9. A TNF-receptor protein according to claim 8, wherein said double point variant proteins possess reduced immunogenicity.

10. A TNF-receptor protein according to claims 1, wherein said TNF-receptor protein is PEGylated.

11. A TNF-receptor protein according to claim 1, wherein the C-terminal leucine of said amino acids 15–138 of SEQ ID NO: 1 is deleted.

12. A TNF-receptor protein according to claims 1, 2, or 3, wherein two or more TNF-receptor variants are covalently linked via disulfide bonds.

13. A TNF-receptor protein according to claims 1, 2, or 3, wherein two or more TNF-receptor variants are covalently linked via chemical cross linking.

14. A TNF-receptor protein according to claims 1, 2, or 3, wherein two or more TNF-receptor variants are covalently linked by a linker peptide.

15. A TNF-receptor protein according to claim 14, wherein said linker peptide is a sequence of at least one and not more than about 30 amino acid residues.

16. A TNF-receptor protein according to claim 14, wherein said linker peptide is a sequence of at least 5 and not more than about 20 amino acid residues.

17. A TNF-receptor protein according to claim 16, wherein said linker peptide is a sequence of at least 10 and not more than about 15 amino acid residues.

18. A TNF-receptor protein according to claims 14, wherein the linker peptide comprises one or more of the following amino acid residues: Gly, Ser, Ala, or Thr.

19. A pharmaceutical composition comprising a TNF-receptor protein according to claim 1 and a pharmaceutical carrier.

* * * * *

```
                              SEQUENCE LISTING

<160> NUMBER OF SEQ ID NOS: 7

<210> SEQ ID NO 1
<211> LENGTH: 175
<212> TYPE: PRT
<213> ORGANISM: Artificial sequence
<220> FEATURE:
<223> OTHER INFORMATION: synthetically engineered TNF-R extra-cellular
      domain variant
<220> FEATURE:
<221> NAME/KEY: SIGNAL
<222> LOCATION: (15)..(35)
<220> FEATURE:
<221> NAME/KEY: mat_peptide
<222> LOCATION: (16)..()

<400> SEQUENCE: 1

Met Gly Leu Ser Thr Val Pro Asp Leu Leu Leu Pro Leu Val Leu Leu
-15                 -10                 -5                  -1  1

Glu Leu Leu Val Gly Ile Tyr Pro Ser Gly Val Ile Gly Cys Pro Gln
            5                   10                  15

Gly Lys Tyr Ile His Pro Gln Asn Asn Ser Ile Cys Cys Thr Lys Cys
        20                  25                  30

His Lys Gly Thr Tyr Leu Tyr Asn Asp Cys Pro Gly Pro Gly Gln Asp
    35                  40                  45

Thr Asp Cys Arg Glu Cys Glu Ser Gly Ser Phe Thr Ala Ser Glu Asn
50                  55                  60                  65
```

-continued

```
His Leu Arg His Cys Leu Ser Cys Ser Lys Cys Arg Lys Glu Met Gly
             70                  75                  80

Gln Val Glu Ile Ser Ser Cys Thr Val Asp Arg Asp Thr Val Cys Gly
         85                  90                  95

Cys Arg Lys Asn Gln Tyr Arg His Tyr Trp Ser Glu Asn Leu Phe Gln
        100                 105                 110

Cys Phe Asn Cys Ser Leu Cys Leu Asn Gly Thr Val His Leu Ser Cys
    115                 120                 125

Gln Glu Lys Gln Asn Thr Val Cys Thr Asp Tyr Lys Asp His Asp Gly
130                 135                 140                 145

Asp Tyr Lys Asp His Asp Ile Asp Tyr Lys Asp Asp Asp Lys
                150                 155                 160

<210> SEQ ID NO 2
<211> LENGTH: 8
<212> TYPE: PRT
<213> ORGANISM: Homo sapiens

<400> SEQUENCE: 2

Ile Tyr Pro Ser Gly Val Ile Gly
1               5

<210> SEQ ID NO 3
<211> LENGTH: 14
<212> TYPE: PRT
<213> ORGANISM: Homo sapiens

<400> SEQUENCE: 3

Leu Val Pro His Leu Gly Asp Arg Glu Lys Arg Asp Ser Val
1               5                   10

<210> SEQ ID NO 4
<211> LENGTH: 5
<212> TYPE: PRT
<213> ORGANISM: Artificial sequence
<220> FEATURE:
<223> OTHER INFORMATION: linker consensus sequence

<400> SEQUENCE: 4

Gly Ser Gly Gly Ser
1               5

<210> SEQ ID NO 5
<211> LENGTH: 5
<212> TYPE: PRT
<213> ORGANISM: Artificial sequence
<220> FEATURE:
<223> OTHER INFORMATION: linker consensus sequence

<400> SEQUENCE: 5

Gly Gly Gly Gly Ser
1               5

<210> SEQ ID NO 6
<211> LENGTH: 4
<212> TYPE: PRT
<213> ORGANISM: Artificial sequence
<220> FEATURE:
<223> OTHER INFORMATION: linker consensus sequence

<400> SEQUENCE: 6

Gly Gly Gly Ser
1
```

<210> SEQ ID NO 7
<211> LENGTH: 175
<212> TYPE: PRT
<213> ORGANISM: Artificial sequence
<220> FEATURE:
<223> OTHER INFORMATION: synthetically engineered TNF-R extra-cellular domain variant
<220> FEATURE:
<221> NAME/KEY: SIGNAL
<222> LOCATION: (1)..(21)
<220> FEATURE:
<221> NAME/KEY: mat_peptide
<222> LOCATION: (30)..()

<400> SEQUENCE: 7

```
Met Gly Leu Ser Thr Val Pro Asp Leu Leu Leu Pro Leu Val Leu Leu
                -25                 -20                 -15
Glu Leu Val Gly Ile Tyr Pro Ser Gly Val Ile Gly Cys Pro Gln
            -10                  -5                  -1   1
Gly Lys Tyr Ile His Pro Gln Asn Asn Ser Ile Cys Cys Thr Lys Cys
         5                  10                  15
His Lys Gly Thr Tyr Leu Tyr Asn Asp Cys Pro Gly Pro Gly Gln Asp
 20                  25                  30                  35
Thr Asp Cys Arg Glu Cys Glu Ser Gly Ser Phe Thr Ala Ser Glu Asn
                 40                  45                  50
His Leu Arg His Cys Leu Ser Cys Ser Lys Cys Arg Lys Glu Met Gly
                 55                  60                  65
Gln Val Glu Ile Ser Ser Cys Thr Val Asp Arg Asp Thr Val Cys Gly
                 70                  75                  80
Cys Arg Lys Asn Gln Tyr Arg His Tyr Trp Ser Glu Asn Leu Phe Gln
 85                  90                  95
Cys Phe Asn Cys Ser Leu Cys Leu Asn Gly Thr Val His Leu Ser Cys
100                 105                 110                 115
Gln Glu Lys Gln Asn Thr Val Cys Thr Asp Tyr Lys Asp His Asp Gly
                120                 125                 130
Asp Tyr Lys Asp His Asp Ile Asp Tyr Lys Asp Asp Asp Lys
                135                 140                 145
```